US008710261B2

(12) United States Patent
Palle et al.

(10) Patent No.: US 8,710,261 B2
(45) Date of Patent: Apr. 29, 2014

(54) 5-PHENYL-PENTANOIC ACID DERIVATIVES AS MATRIX METALLOPROTEINASE INHIBITORS FOR THE TREATMENT OF ASTHMA AND OTHER DISEASES

(75) Inventors: Venkata P. Palle, Pune (IN); Viswajanani Jitendra Sattigeri, Gurgaon (IN); Manoj Kumar Khera, Gurgaon (IN); Sreedhara Rao Voleti, Gurgaon (IN); Abhijit Ray, New Delhi (IN); Sunanda G. Dastidar, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 1321 days.

(21) Appl. No.: 11/816,836

(22) PCT Filed: Feb. 21, 2006

(86) PCT No.: PCT/IB2006/000349
§ 371 (c)(1),
(2), (4) Date: Feb. 13, 2008

(87) PCT Pub. No.: WO2006/090235
PCT Pub. Date: Aug. 31, 2006

(65) Prior Publication Data
US 2008/0194565 A1 Aug. 14, 2008

(30) Foreign Application Priority Data
Feb. 22, 2005 (IN) .............................. 380/DEL/2005

(51) Int. Cl.
| | |
|---|---|
| C07D 253/08 | (2006.01) |
| C07D 239/54 | (2006.01) |
| C07D 239/64 | (2006.01) |
| C07D 239/96 | (2006.01) |
| C07D 249/18 | (2006.01) |
| C07D 209/48 | (2006.01) |
| C07D 209/12 | (2006.01) |
| C07D 237/32 | (2006.01) |
| C07D 401/10 | (2006.01) |
| C07D 403/10 | (2006.01) |
| C07D 471/04 | (2006.01) |
| A61K 31/53 | (2006.01) |
| A61P 19/02 | (2006.01) |
| A61P 11/06 | (2006.01) |
| C07D 213/64 | (2006.01) |
| C07D 265/28 | (2006.01) |
| C07D 211/88 | (2006.01) |
| C07D 207/40 | (2006.01) |
| C07D 263/58 | (2006.01) |

(52) U.S. Cl.
USPC ........... 562/433; 562/475; 562/405; 562/400; 514/568; 514/243; 544/183; 544/180

(58) Field of Classification Search
USPC .......... 562/433, 470, 405, 400; 514/568, 243; 544/183
See application file for complete search history.

(56) References Cited

U.S. PATENT DOCUMENTS 6,350,885 B1  2/2002  O'Brien et al. ................ 549/460

FOREIGN PATENT DOCUMENTS

| CA | 2538315 | 3/2005 | |
|---|---|---|---|
| WO | WO 91/03243 | 3/1991 | ........... A61K 31/445 |

(Continued)

OTHER PUBLICATIONS

Hashizume et al. Heterocycles 38(7), 1551-1571, 1994; CA 121: 255537, 1994. CAPLUS Abstract provided.*

(Continued)

*Primary Examiner* — Venkataraman Balasubramanian

(57) ABSTRACT

The present invention relates to Compounds having the structure of Formula I: wherein n is an integer from 1 to 5; $R_1$ is optionally substituted alkyl, alkenyl, alkynyl, cycloalkyl, aryl, heterocyclyl, heteroaryl, aralkyl, alkoxy, aryloxy, alkenyloxy or alkynyloxy; $R_2$ is alkenyl, allcynyl, aryl, heterocyclyl, heteroaryl, cycloalkyl, $NR_4R_5$, —$NHC(=Y)R_4$, —$NHC(=Y)NR_5R_x$, —$NHC(=O)OR_4$, —$NHSO_2R_4$, $C(=Y)NR_4R_5$, $C(=O)OR_6$ [wherein Y is oxygen or sulphur], $OR_5$, —$O(C=O)NR_4R_5$, O-acyl, $S(O)_mR_4$, —$SO_2N(R_4)_2$, cyano, amidino or guanidino [wherein $R_4$ is alkyl, alkenyl, alkynyl, cycloalkyl, aryl, heterocyclyl, heteroaryl, aralkyl, heteroarylalkyl, heterocyclylalkyl or cycloalkylalkyl and m is an integer 0-2; $R_5$ is hydrogen or $R_4$; $R_x$ is $R_4$ or —$SO_2N(R_4)_2$ and $R_6$ is hydrogen, alkyl, cycloalkyl, aralkyl, heteroarylalkyl, heterocyclylalkyl or cycloalkylalkyl]; $R_3$ is hydrogen, fluorine, alkyl, cycloalkylalkyl or aralkyl; A is OH, $OR_4$, —$OC(=O)NR_4R_5$, O-acyl, $NH_2$, $NR_4R_5$, —NHC (=Y)$R_4$, —$NHC(=Y)NR_5R_x$, —$NHC(=O)OR_4$, —$NHSO_2R_4$, and to processes for the synthesis of the same. This invention also relates to pharmacological compositions containing the compounds of the present invention, and methods of treating asthma, rheumatoid arthritis, COPD, rhinitis, osteoarthritis, psoriatic arthritis, psoriasis, pulmonary fibrosis pulmonary inflammation, acute respiratory distress syndrome, perodontitis, multiple sclerosis, gingivitis, atherosclerosis, neointimal proliferation, which leads to restenosis and ischemic heart failure, stroke, renal diseases, tumor metastasis, and other inflammatory disorders characterized by overexpression and over-activation of an matrix metalloproteinase, using the compounds.

(I)

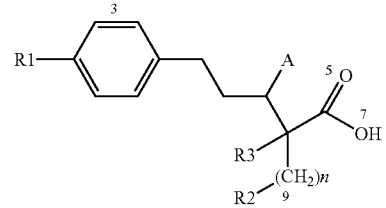

9 Claims, No Drawings

(56) References Cited

FOREIGN PATENT DOCUMENTS

| WO | WO 94/12181 | 6/1994 | ............ A61K 31/445 |
|---|---|---|---|
| WO | WO 96/15096 | 5/1996 | .............. C07C 59/88 |
| WO | WO 96/32377 | 10/1996 | ............ C07C 275/64 |
| WO | WO 98/09940 | 3/1998 | ............ C07C 251/48 |
| WO | WO 98/56899 | 12/1998 | ................ C12N 9/08 |
| WO | WO 03/011808 | 2/2003 | .............. C07C 62/32 |
| WO | WO 2004/091613 | 10/2004 | .............. A61K 31/44 |
| WO | WO 2004/110974 | 12/2004 | .............. C07C 59/48 |
| WO | WO 2004/113279 | 12/2004 | ............ C07C 311/08 |
| WO | WO 2005/026120 | 3/2005 | ............ C07D 209/48 |
| WO | WO 2006/090235 | 8/2006 | ............ C07D 249/18 |

OTHER PUBLICATIONS

Demedts, et al., Thorax 2006;61:196-201.*

Kelly, et al., Current Opinion in Pulmonary Medicine. 9(1):28-33, Jan. 2003.*

Dorman, et al., Recent Patents on Cardiovascular Drug Discovery, 2007, 2, 000-000.*

Murphy, et al., Nature Clin. Practice Rheumatology (2008)4, 128-135.*

Johnson, et al., PNAS, Oct. 25, 2005 vol. 102 No. 43 15575-15580.*

Borkakoti, Biochemical Society Transactions (2004) vol. 32, part 1, 17-20.*

Cecil Textbook of Medicine, edited by Bennet, J.C., and Plum F., 20th edition, vol. 1, 1004-1010, 1996.*

Whittaker et al., "Design and Therapeutic Application of Matrix Metalloproteinase Inhibitors", *Chemical Reviews*, 99(9):2735-2776 (1999).

Barron et al., "Synthesis and Antiinflammatory activity of 4-(*p*-Biphenylyl)-3-hydroxybutyric Acid and Related Compounds", *Journal of Medicinal Chemistry*, 11(6):1139-1144 (1968).

Greene, T.Q. and Wuts, P.G.M., 1991. *Protective Groups in Organic Synthesis*. 2nd Edition. New York: Wiley Interscience Publications.

Moscoso A., Raul, *Intellectual Property and Innovation in Ecuador*, Abya Yala. Quito (2000) p. 37-38.

Goodman & Gilman, Pharmacological Bases of Therapeutics, 9th ed., McGraw-Hill Interamericana, Mexico (1996), 1:p. 47-48.

Jose Manual Otero Lastres, Invention and exceptions to patentability under Decision 486, Seminar on Patents, Quito (2000) p. 31.

Bercovitz, A. 1969. Los Requisitos Positivos de Patentabilidad en el Derecho Aleman. Thesis (doctoral). University of Madrid. pp. 144-145.

Fernández-Novoa and Gómez Segade, 1984. La Modernizacion del Derecho Español de Patentes. Madrid:Editorial Montecorvo, S.A. p. 8.

* cited by examiner

5-PHENYL-PENTANOIC ACID DERIVATIVES AS MATRIX METALLOPROTEINASE INHIBITORS FOR THE TREATMENT OF ASTHMA AND OTHER DISEASES

FIELD OF THE INVENTION

The present invention relates to certain beta hydroxy acids and to processes for the synthesis of the same. This invention also relates to pharmacological compositions containing the compounds of the present invention, and methods of treating asthma, rheumatoid arthritis, COPD, rhinitis, osteoarthritis, psoriatic arthritis, psoriasis, pulmonary fibrosis, pulmonary inflammation, acute respiratory distress syndrome, perodontitis, multiple sclerosis, gingivitis, atherosclerosis, neointimal proliferation, which leads to restenosis and ischemic heart failure, stroke, renal diseases, tumor metastasis, and other inflammatory disorders characterized by over-expression and over-activation of an matrix metalloproteinase, using the compounds.

BACKGROUND OF THE INVENTION

Metalloproteinases (MMPs) are a naturally occurring superfamily of proteinases (enzymes) found in most mammals. The superfamily is composed of at least 26 members of zinc-containing enzymes produced by many cell types and sharing structural and functional features. Based on structural and functional considerations proteinases have been classified into different families and subfamilies (Hopper, N M, 1994, FEBS) such as collagenases (MMP-1, MMP-13), gelatinases (MMP-2, MMP-9), metalloelastases (MMP-12), the MT-MMPs (MMP-14, MMP-15) and sheddases such as TNF-converting enzymes (TACE, ACE).

Metalloproteinases are believed to be important in a plethora of physiological disease processes that involve remodeling such as embryonic development, bone formation and uterine remodeling during menstruation. One major biological function of MMPs is to catalyze the breakdown of connective tissues or extra-cellular matrix by their ability to hydrolyze various components of tissue or matrix. Apart from their role in degrading connective tissue, MMPs are always involved in the activation of zymogen (pro) forms of other MMPs thereby inducing MMP activation. They are also involved in biosynthesis of TNF-alpha which is implicated in many pathological conditions.

MMP-12 also known as macrophage elastase or metalloelastase is expressed in activated macrophages and has been shown to be secreted from alveolar macrophages from smokers as well as in foam cells in atherosclerotic lesions. MMP-12 knockout mouse studies have shown the development of significant emphysema, thus supporting its role in COPD. MMP-9 (gelatinase B, 92 kDa type IV collagenase) is one member of the MMP family that is released as a proenzyme and subsequently activated via a protease cascade in vivo. The concentration of MMP-9 is increased in diseases like asthma, interstitial pulmonary fibrosis (IPF), adult respiratory distress syndrome (ARDS), and in chronic obstructive pulmonary disease (COPD). Because of its proteolytic ability, MMP-9 has been implicated in tissue remodelling of the airways and lungs in chronic inflammatory diseases such as severe asthma and COPD. MMP-9 is also likely to be physiologically important because of its ability to regulate the digestion of components of the extracellular matrix as well as the activity of other proteases and cytokines. MMP-9 is secreted in neutrophils, macrophages, osteoclasts, which are easily induced by cytokines and growth factors, and plays a role in various physiological and pathological processes.

Over-expression or over-activation of an MMP or an imbalance between an MMP and a natural (i.e., endogenous) tissue inhibitor of a matrix metalloproteinase (TIMP) has been linked to a pathogenesis of diseases characterized by the breakdown of connective tissue or extracellular matrix.

Examples of inflammatory conditions and autoimmune disorders in which the compounds of the invention have potentially beneficial effects include diseases of the respiratory tract such as asthma (including allergen-induced asthmatic reactions), cystic fibrosis, bronchitis (including chronic bronchitis), chronic obstructive pulmonary disease (COPD), adult respiratory distress syndrome (ARDS), chronic pulmonary inflammation, rhinitis and upper respiratory tract inflammatory disorders (URID), ventilator induced lung injury, silicosis, pulmonary sarcoidosis, idiopathic pulmonary fibrosis, bronchopulmonary dysplasia, arthritis e.g., rheumatoid arthritis, osteoarthritis, infectious arthritis, psoriasis arthritis, traumatic arthritis, rubella arthritis, Reiter's syndrome, gouty arthritis and prosthetic joint failure gout acute synovitis, spondylitis and non-articular inflammatory conditions, e.g., herniated/ruptured/prolapsed intervertebral disk syndrome, bursitis, tendonitis, tenosynovitic fibromyalgic syndrome and other inflammatory conditions associated with ligamentous sprain and regional musculoskeletal strain, inflammatory disorders of the gastrointestinal tract, e.g., ulcerative colitis, diverticulitis, Crohn's disease, inflammatory bowel diseases, irritable bowel syndrome and gastritis, multiple sclerosis, systemic lupus erythematosus sclerodenna, autoimmune exocrinopathy, autoimmune encephalomyelitis, diabetes, tumor angiogenesis and metastasis, cancer including carcinoma of the breast, colon, rectum, lung, kidney, ovary, stomach, uterus, pancreas, liver, oral, laryngeal and prostate, melanoma, acute and chronic leukemia, periodontal disease, neurodegenerative disease Alzheimer's disease, Parkinson's disease, epilepsy, muscle degeneration, inguinal hernia retinal degeneration, diabetic retinopathy, macular degeneration, ocular inflammation, bone desorption diseases, osteoporosis, osteopetrosis, graft vs. host reaction allograft rejections, sepsis, endotoxemia, toxic shock syndrome, tuberculosis, usual interstitial and cryptogenic organizing pneumonia, bacterial meningitis, systemic cachexia, cachexia secondary to infection or malignancy, cachexia secondary to acquired immune deficiency syndrome (AIDS), malaria, leprosy, leishmaniasis, Lyme disease, glomerulonephritis, glomerulosclerosis, renal fibrosis, liver fibrosis, pancreatitis, hepatitis, endometriosis, pain, e.g., that associated with inflammation and/or trauma, inflammatory diseases of the skin, e.g., dermatitis, dermatitis, skin ulcers, psoriasis, eczema, systemic valvulitis vascular dementia, thrombosis, atherosclerosis, restenosis, reperfusion injury, plaque calcification, myocarditis, aneurysm, stroke, pulmonary hypertension, left ventricular remodeling and heart failure. Diseases of principal interest include COPD and inflammatory diseases of the respiratory tract and joints and vascular diseases. It will be appreciated by those skilled in the art that reference herein to treatment extends to prophylaxis as well as the treatment of established conditions.

Inhibition of the activity of one or more MMPs may be of benefit in these diseases or conditions, for example, various inflammatory and allergic diseases such as, inflammation of the joint, inflammation of the GI tract, inflammation of the skin, collagen remodeling, etc.

Research has been carried out into the identification of inhibitors that are selective e.g., for a few of the MMP subtypes. An MMP inhibitor of improved selectivity would avoid potential side effects associated with inhibition of MMPs that are not involved in the pathogenesis of the disease being treated. Further, use of more selective MMP inhibitors would require administration of a lower amount of the inhibitor for treatment of disease than would otherwise be required and, after administration, partitioned in vivo among multiple MMPs. Still further, the administration of a lower amount of compound would improve the margin of safety between the dose of the inhibitor required for therapeutic activity and the dose of the inhibitor at which toxicity is observed.

The design and therapeutic application of MMP inhibitors has revealed that the requirement of a molecule to be an effective inhibitor of MMP class of enzymes is a functional group (e.g., carboxylic acid, hydroxamic acid or sulphydryl) capable of chelating to the active site $Zn^{2+}$ ion (Whittaker, et al., *Chem Rev.*, 1999, 99, 2735-76).

WO 04/110974 discloses compounds and their physiologically functional derivatives as inhibitors of matrix metalloproteinase enzymes. WO 04/113279 discloses inhibitors of matrix metalloproteinase. U.S. Pat. No. 6,350,885 discloses tricyclic heteroaromatic compounds and their derivatives as inhibitors of matrix metalloproteinases. WO 98/09940 discloses biphenyl butyric acids and their derivatives as inhibitors of matrix metalloproteinases. *J. Med. Chem.*, 1968, vol. 11(6), 1139-1144 discloses synthesis and anti-inflammatory activity of 4-(p-biphenylyl)-3-hydroxybutyric acid and related compounds. WO 96/15096 discloses substituted 4-biarylbutyric or 5-biarylpentanoic acids and derivatives as matrix metalloproteinase inhibitors.

SUMMARY OF THE INVENTION

The present invention discloses a novel class of compounds that are dual MMP-9/12 inhibitors and have desirable activity profiles. The compounds of this invention have beneficial potency, selectivity and/or pharmacokinetic properties.

In one aspect, there are provided matrix metalloprotease inhibitors, which can be useful as safe and effective therapeutic or prophylactic agents for the treatment of various inflammatory and allergic diseases. Also provided are processes for synthesizing such compounds.

In another aspect, pharmaceutical compositions containing such compounds are provided together with acceptable carriers, excipients or diluents, which can be useful for the treatment of inflammatory and autoimmune diseases.

The racemates, enantiomers, diastereomers, rotational isomers, N-oxides, polymorphs, pharmaceutically acceptable salts and pharmaceutically acceptable solvates of these compounds, prodrugs and metabolites having the same type of activity are also provided, as well as pharmaceutical compositions comprising the compounds, their metabolites, racemates, enantiomers, diastereomers, conformational isomers, N-oxides, polymorphs, solvates or pharmaceutically acceptable salts thereof, in combination with a pharmaceutically acceptable carrier and optionally included excipients.

Other aspects will be set forth in the description which follows, and in part will be apparent from the description or may be learnt by the practice of the invention.

In accordance with one aspect, there are provided compounds having the structure of Formula I:

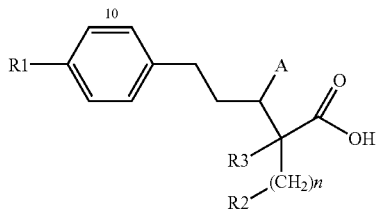

Formula I wherein
n is an integer from 1 to 5;
$R_1$ can be optionally substituted alkyl, alkenyl, alkynyl, cycloalkyl, aryl, heterocyclyl, heteroaryl, aralkyl, alkoxy, aryloxy, alkenyloxy or alkynyloxy;

$R_2$ can be alkenyl, alkynyl, aryl, heterocyclyl, heteroaryl, cycloalkyl, $NR_4R_5$, $—NHC(=Y)R_4$, $—NHC(=Y)NR_5R_x$, $—NHC(=O)OR_4$, $—NHSO_2R_4$, $C(=Y)NR_4R_5$, $C(=O)OR_6$ [wherein Y can be oxygen or sulphur], $OR_5$, $—OC(=O)NR_4R_5$, O-acyl, $S(O)_mR_4$, $—SO_2N(R_4)_2$, cyano, amidino or guanidino [wherein $R_4$ can be alkyl, alkenyl, alkynyl, cycloalkyl, aryl, heterocyclyl, heteroaryl, aralkyl, heteroarylalkyl, heterocyclylalkyl or cycloalkylalkyl and m is an integer 0-2; $R_5$ can be hydrogen or $R_4$; $R_x$ can be $R_4$ or $—SO_2N(R_4)_2$ and $R_6$ is hydrogen, alkyl, cycloalkyl, aralkyl, heteroarylalkyl, heterocyclylalkyl or cycloalkylalkyl];
$R_3$ can be hydrogen, fluorine, alkyl, cycloalkylalkyl or aralkyl;
A can be OH, $OR_4$, $—OC(=O)NR_4R_5$, O-acyl, $NH_2$, $NR_4R_5$, $—NHC(=Y)R_4$, $—NHC(=Y)NR_5R_x$, $—NHC(=O)OR_4$, $—NHSO_2R_4$.

In one embodiment, the invention relates to compounds of general Formula Ia,

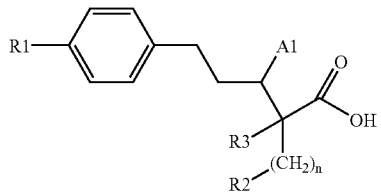

Formula Ia wherein
A1 can be OH, $—OC(=O)NR_4R_5$, $NH_2$, $NR_4R_5$, $—NHC(=Y)R_4$, $—NHC(=Y)NR_5R_x$, $—NHC(=O)OR_4$, $—NHSO_2R_4$;
n, $R_1$, $R_2$, $R_3$ and $R_4$ can be as defined earlier.

In another embodiment, the invention relates to compounds of general Formula Ib,

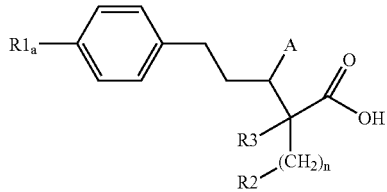

Formula Ib wherein
$R_{1a}$ can be aryl or heteroaryl;
n, $R_2$, $R_3$ and A can be as defined earlier.

In another embodiment, the invention relates to compounds of general Formula Ic,

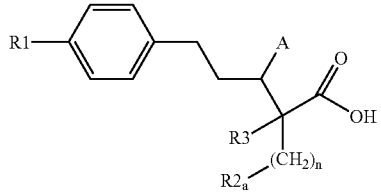

Formula Ic wherein
$R_{2a}$ can be $NR_4R_5$, $—NHC(=Y)R_4$, $—NHC(=Y)NR_5R_x$, $—NHC(=O)OR_4$, $—NHSO_2R_4$, amidino or guanidino

[wherein Y can be oxygen or sulphur and $R_4$ can be alkyl, alkenyl, alkynyl, cycloalkyl, aryl, heterocyclyl, heteroaryl, aralkyl, heteroarylalkyl, heterocyclylalkyl or cycloalkylalkyl and m is an integer 0-2; $R_5$ is hydrogen or $R_4$; $R_4$ and $R_5$ together may optionally form a heterocyclic ring containing one or more heteroatoms such as O, N or S and $R_x$ is $R_4$ or $—SO_2N(R_4)_2$];

n, $R_1$, $R_3$ and A can be as defined earlier.

In yet another embodiment, the invention encompasses compounds that include, for example 5-Biphenyl-4-yl-3-hydroxy-2-[2-(4-oxo-1,2,3-benzotriazin-3(4H)-yl)ethyl]pentanoic acid (Compound No. 1), 5-(4'-tert-Butylbiphenyl-4-yl)-2-[2-(1,3-dioxo-1,3-dihydro-2H-isoindol-2-yl)ethyl]-3-hydroxypentanoic acid (Compound No. 2), 5-(4'-Butylbiphenyl-4-yl)-2-[2-(1,3-dioxo-1,3-dihydro-2H-isoindol-2-yl)ethyl]-3-hydroxypentanoic acid (Compound No. 3), 5-(4'-Chlorobiphenyl-4-yl)-2-[2-(1,3-dioxo-1,3-dihydro-2H-isoindol-2-yl)ethyl]-3-hydroxypentanoic acid (Compound No. 4), 2-[2-(1,3-Dioxo-1,3-dihydro-2H-isoindol-2-yl)ethyl]-3-hydroxy-5-(4'-trifluoromethoxybiphenyl-4-yl)pentanoic acid (Compound No. 5), 2-[2-(1,3-Dioxo-1,3-dihydro-2H-isoindol-2-yl)ethyl]-5-(4'-ethoxybiphenyl-4-yl)-3-hydroxypentanoic acid (Compound No. 6), 2-[2-(1,3-Dioxo-1,3-dihydro-2H-isoindol-2-yl)ethyl]-5-(4'-formylbiphenyl-4-yl)-3-hydroxypentanoic acid (Compound No. 7), 2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 8), 2-[2-(1,3-Dioxo-1,3-dihydro-2H-isoindol-2-yl)ethyl]-3-hydroxy-5-(4'-propoxybiphenyl-4-yl)pentanoic acid (Compound No. 9), 5-(3',4'-Difluorobiphenyl-4-yl)-2-[2-(1,3-dioxo-1,3-dihydro-2H-isoindol-2-yl)ethyl]-3-hydroxypentanoic acid (Compound No. 10), 2-(2-{[(Benzyloxy)carbonyl]amino}ethyl)-5-biphenyl-4-yl-3-hydroxypentanoicacid (Compound No. 11).

5-Biphenyl-4-yl-2-[2-(1,3-dioxo-1,3-dihydro-2H-isoindol-2-yl)ethyl]-3-hydroxypentanoic acid (Compound No. 12), (2R,3S+2S,3R)-2-[2-(1,3-Dioxo-1,3-dihydro-2H-isoindol-2-yl)ethyl]-5-(4'-formylbiphenyl-4-yl)-3-hydroxypentanoic acid (Compound No. 13), (2R,3R+2S,3S)-2-[2-(1,3-Dioxo-1,3-dihydro-2H-isoindol-2-yl)ethyl]-5-(4'-formylbiphenyl-4-yl)-3-hydroxypentanoic acid (Compound No. 14), (2R,3R+2S,3S)-2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 15), (2R,3S+2S,3R)-2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 16), (2R,3S+2S,3R)-5-(4'-Acetylbiphenyl-4-yl)-2-[2-(1,3-dioxo-1,3-dihydro-2H-isoindol-2-yl)ethyl]-3-hydroxypentanoic acid (Compound No. 17), (2R,3R+2S,3S)-5-(4'-Acetylbiphenyl-4-yl)-2-[2-(1,3-dioxo-1,3-dihydro-2H-isoindol-2-yl)ethyl]-3-hydroxypentanoic acid (Compound No. 18), (2R,3S+2S,3R)-2-[2-(1,3-Dioxo-1,3-dihydro-2H-isoindol-2-yl)ethyl]-3-hydroxy-5-(4'-propoxybiphenyl-4-yl)pentanoic acid (Compound No. 19), (2R,3R+2S,3S)-2-[2-(1,3-Dioxo-1,3-dihydro-2H-isoindol-2-yl)ethyl]-3-hydroxy-5-(4'-propoxybiphenyl-4-yl)pentanoic acid (Compound No. 20), (2R,3S+2S,3R)-5-(3',4'-Difluorobiphenyl-4-yl)-2-[2-(1,3-dioxo-1,3-dihydro-2H-isoindol-2-yl)ethyl]-3-hydroxypentanoic acid (Compound No. 21), (2R,3R+2S,3S)-5-(3',4'-Difluorobiphenyl-4-yl)-2-[2-(1,3-dioxo-1,3-dihydro-2H-isoindol-2-yl)ethyl]-3-hydroxypentanoic acid (Compound No. 22), 2-[2-(1,3-Dioxo-1,3-dihydro-2H-isoindol-2-yl)ethyl]-3-hydroxy-5-(4'-methoxybiphenyl-4-yl)pentanoic acid (Compound No. 23), 5-(2',3'-Dimethylbiphenyl-4-yl)-2-[2-(1,3-dioxo-1,3-dihydro-2H-isoindol-2-yl)ethyl]-3-hydroxypentanoic acid (Compound No. 24), 2-[2-(1,3-Dioxo-1,3-dihydro-2H-isoindol-2-yl)ethyl]-3-hydroxy-5-[3'-(trifluoromethyl)biphenyl-4-yl]pentanoic acid (Compound No. 25), 2-[2-(1,3-Dioxo-1,3-dihydro-2H-isoindol-2-yl)ethyl]-5-(4'-ethylbiphenyl-4-yl)-3-hydroxypentanoic acid (Compound No. 26), 5-(3',5'-Dichlorobiphenyl-4-yl)-2-[2-(1,3-dioxo-1,3-dihydro-2H-isoindol-2-yl)ethyl]-3-hydroxypentanoic acid (Compound No. 27), 5-[4'-Chloro-3'-(trifluoromethyl)biphenyl-4-yl]-2-[2-(1,3-dioxo-1,3-dihydro-2H-isoindol-2-yl)ethyl]-3-hydroxypentanoic acid (Compound No. 28), 5-(2',5'-Difluorobiphenyl-4-yl)-2-[2-(1,3-dioxo-1,3-dihydro-2H-isoindol-2-yl)ethyl]-3-hydroxypentanoic acid (Compound No. 29), 2-[2-(1,3-Dioxo-1,3-dihydro-2H-isoindol-2-yl)ethyl]-3-hydroxy-5-[2'-(trifluoromethoxy)biphenyl-4-yl]pentanoic acid (Compound No. 30), 2-[2-(1,3-Dioxo-1,3-dihydro-2H-isoindol-2-yl)ethyl]-3-hydroxy-5-[4'-(methylthio)biphenyl-4-yl]pentanoic acid (Compound No. 31), 2-[2-(1,3-Dioxo-1,3-dihydro-2H-isoindol-2-yl)ethyl]-5-(4'-fluoro-3'-methylbiphenyl-4-yl)-3-hydroxypentanoic acid (Compound No. 32), 2-[2-(1,3-Dioxo-1,3-dihydro-2H-isoindol-2-yl)ethyl]-3-hydroxy-5-(3'-isopropylbiphenyl-4-yl)pentanoic acid (Compound No. 33), 5-(3',4'-Dimethylbiphenyl-4-yl)-2-[2-(1,3-dioxo-1,3-dihydro-2H-isoindol-2-yl)ethyl]-3-hydroxypentanoic acid (Compound No. 34), 5-(2',6'-Difluorobiphenyl-4-yl)-2-[2-(1,3-dioxo-1,3-dihydro-2H-isoindol-2-yl)ethyl]-3-hydroxypentanoic acid (Compound No. 35), 2-[2-(1,3-Dioxo-1,3-dihydro-2H-isoindol-2-yl)ethyl]-5-(4'-fluorobiphenyl-4-yl)-3-hydroxypentanoic acid (Compound No. 36), 5-(3',5'-Difluorobiphenyl-4-yl)-2-[2-(1,3-dioxo-1,3-dihydro-2H-isoindol-2-yl)ethyl]-3-hydroxypentanoic acid (Compound No. 37), 5-(3'-Chloro-4'-fluorobiphenyl-4-yl)-2-[2-(1,3-dioxo-1,3-dihydro-2H-isoindol-2-yl)ethyl]-3-hydroxypentanoic acid (Compound No. 38), 5-(3',4'-Dimethoxybiphenyl-4-yl)-2-[2-(1,3-dioxo-1,3-dihydro-2H-isoindol-2-yl)ethyl]-3-hydroxypentanoic acid (Compound No. 39), 5-(3'-Chlorobiphenyl-4-yl)-2-[2-(1,3-dioxo-1,3-dihydro-2H-isoindol-2-yl)ethyl]-3-hydroxypentanoic acid (Compound No. 40), 2-[2-(1,3-Dioxo-1,3-dihydro-2H-isoindol-2-yl)ethyl]-3-hydroxy-5-(3'-methylbiphenyl-4-yl)pentanoic acid (Compound No. 41), 5-(2',3'-Difluorobiphenyl-4-yl)-2-[2-(1,3-dioxo-1,3-dihydro-2H-isoindol-2-yl)ethyl]-3-hydroxypentanoic acid (Compound No. 42), 2-[2-(1,3-Dioxo-1,3-dihydro-2H-isoindol-2-yl)ethyl]-5-(2'-fluoro-3'-methoxybiphenyl-4-yl)-3-hydroxypentanoic acid (Compound No. 43), 2-[2-(1,3-Dioxo-1,3-dihydro-2H-isoindol-2-yl)ethyl]-5-(3'-fluoro-4'-methylbiphenyl-4-yl)-3-hydroxypentanoic acid (Compound No. 44), 5-Biphenyl-4-yl-3-hydroxy-2-{2-[(phenylacetyl)amino]ethyl}pentanoic acid (Compound No. 45), 2-(3-Biphenyl-4-yl-1-hydroxypropyl)-6-(1,3-dioxo-1,3-dihydro-2H-isoindol-2-yl)hexanoic acid (Compound No. 46), 5-Biphenyl-4-yl-3-hydroxy-2-[2-(1-oxophthalazin-2(1H)-yl)ethyl]pentanoic acid (Compound No. 47), 5-Biphenyl-4-yl-2-[3-(1,3-dioxo-1,3-dihydro-2H-isoindol-2-yl)propyl]-3-hydroxypentanoic acid (Compound No. 48), 5-Biphenyl-4-yl-3-hydroxy-2-[2-(2'-oxospiro[cyclopropane-1,3'-indol]-1'(2'H)-yl)ethyl]pentanoic acid (Compound No. 49), 2-[2-(1,3-Dioxo-1,3-dihydro-2H-isoindol-2-yl)ethyl]-3-hydroxy-5-(4'-hydroxybiphenyl-4-yl)pentanoic acid (Compound No. 50), 3-Hydroxy-5-(4'-methoxybiphenyl-4-yl)-2-[2-(3-methyl-2,6-dioxo-3,6-dihydropyrimidin-1(2H)-yl)ethyl]pentanoic acid (Compound No. 51), 5-(4'-Chlorobiphenyl-4-yl)-3-hydroxy-2-[2-(3-methyl-2,6-dioxo-3,6-dihydropyrimidin-1(2H)-yl)ethyl]pentanoic acid (Compound No. 52), 5-(4'-Fluorobiphenyl-4-yl)-3-hydroxy-2-[2-(3-methyl-2,6-dioxo-3,6-dihydropyrimidin-1(2H)-yl)ethyl]pentanoic acid (Compound No. 53), 5-[4-(5-Chloro-2-thienyl)phenyl]-2-[2-(1,3-dioxo-1,3-dihydro-2H-isoindol-2-yl)ethyl]-3-hydroxypentanoic acid (Compound No. 54), 4'-[4-Carboxy-6-(1,3-dioxo-1,3-dihydro-2H-isoindol-2-yl)-3-hydroxyhexyl]biphenyl-4-carboxylic acid (Compound No. 55), 2-[2-(1,3-Dioxo-1,3-dihydro-2H-isoindol-2-yl)ethyl]-3-hydroxy-5-[4'-(methoxycarbonyl)biphenyl-4-yl]pentanoic acid (Compound No. 56), 2-[2-(1,3-Dioxo-1,3-dihydro-2H-isoindol-2-yl)ethyl]-3-hydroxy-5-[4'-(trifluoromethyl)biphenyl-4-yl]pentanoic acid (Compound No. 57), 2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 58), 3-Hydroxy-2-[2-(4-oxo-1,2,3-benzotriazin-3(4H)-yl)ethyl]-5-[4'-(trifluoromethyl)biphenyl-4-yl]pentanoic acid (Compound No. 59), 5-(3',4'-Difluorobiphenyl-4-yl)-3-hydroxy-2-[2-(4-oxo-1,2,3-benzotriazin-3(4H)-yl)ethyl]pentanoic acid (Compound No. 60), 2-[2-(1,3-Dioxo-1,3-dihydro-2H-isoindol-2-yl)ethyl]-5-(3'-fluorobiphenyl-4-yl)-3-hydroxypentanoic acid (Compound No. 61), 5-[4'-(Benzyloxy)-3'-fluorobiphenyl-4-yl]-2-[2-(1,3-dioxo-1,3-dihydro-2H-isoindol-2-yl)ethyl]-3-hydroxypentanoic acid (Compound No. 62), 5-[4'-(Benzyloxy)biphenyl-4-yl]-2-[2-(1,3-dioxo-1,3-dihydro-2H-isoindol-2-yl)ethyl]-3-hydroxypentanoic acid (Compound No. 63), 3-Hydroxy-5-(4'-methoxybiphenyl-4-yl)-2-[2-(4-oxo-1,2,3-benzotriazin-3(4H)-yl)ethyl]pentanoic acid (Compound No. 64), 5-(4'-Chlorobiphenyl-4-yl)-3-hydroxy-2-[2-(4-oxo-1,2,3-benzotriazin-3(4H)-yl)ethyl]pentanoic acid (Compound No. 65), 2-[2-(1,3-Dioxo-1,3-dihydro-2H-isoindol-2-yl)ethyl]-3-hydroxy-5-(4'-methylbiphenyl-4-yl)pentanoic acid (Compound No. 66), 3-Hydroxy-5-[4-(6-methoxypyridin-3-yl)phenyl]-2-[2-(4-oxo-1,2,3-benzotriazin-3(4H)-yl)ethyl]pentanoic acid (Compound No. 67), 3-Hydroxy-5-(4'-methylbiphenyl-4-yl)-2-[2-(5-methyl-1,3-dioxo-1,3-dihydro-2H-isoindol-2-yl)ethyl]pentanoic acid (Compound No. 68), 5-(4'-Chlorobiphenyl-4-yl)-3-hydroxy-2-[2-(5-methyl-1,3-dioxo-1,3-dihydro-2H-isoindol-2-yl)ethyl]pentanoic acid (Compound No. 69), 3-Hydroxy-2-[2-(4-oxo-1,2,3-benzotriazin-3(4H)-yl)ethyl]-5-[4'-(trifluoromethoxy)biphenyl-4-yl]pentanoic acid (Compound No. 70), 5-(4'-Fluorobiphenyl-4-yl)-3-hydroxy-2-[2-(4-oxo-1,2,3-benzotriazin-3(4H)-yl)ethyl]pentanoic acid (Compound No. 71), 3-Hydroxy-5-(4'-methylbiphenyl-4-yl)-2-[2-(4-oxo-1,2,3-benzotriazin-3(4H)-yl)ethyl]pentanoic acid (Compound No. 72), 5-(4'-Cyanobiphenyl-4-yl)-3-hydroxy-2-[2-(4-oxo-1,2,3-benzotriazin-3(4H)-yl)ethyl]pentanoic acid (Compound No. 73), 5-(4'-Fluorobiphenyl-4-yl)-3-hydroxy-2-[2-(5-methyl-1,3-dioxo-1,3-dihydro-2H-isoindol-2-yl)ethyl]pentanoic acid (Compound No. 74), 3-Hydroxy-5-[4-(6-methoxypyridin-3-yl)phenyl]-2-[2-(5-methyl-1,3-dioxo-1,3-dihydro-2H-isoindol-2-yl)ethyl]pentanoic acid (Compound No. 75), 5-(4'-Ethylbiphenyl-4-yl)-3-hydroxy-2-[2-(4-oxo-1,2,3-benzotriazin-3(4H)-yl)ethyl]pentanoic acid (Compound No. 76), 3-Hydroxy-2-[2-(5-methyl-1,3-dioxo-1,3-dihydro-2H-isoindol-2-yl)ethyl]-5-[4'-(trifluoromethyl)biphenyl-4-yl]pentanoic acid (Compound No. 77), (2R,3S+2S,3R)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 78), (2R,3R+2S,3S)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 79), (2R,3R+2S,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 80), (2R,3S+2S,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 81), (2R,3S+2S,3R)-2-[2-(1,3-Dioxo-1,3-dihydro-2H-isoindol-2-yl)ethyl]-5-(4'-fluorobiphenyl-4-yl)-3-hydroxypentanoic acid (Compound No. 82), (2R,3R+2S,3S)-2-[2-(1,3-Dioxo-1,3-dihydro-2H-isoindol-2-yl)ethyl]-5-(4'-fluorobiphenyl-4-yl)-3-hydroxypentanoic acid (Compound No. 83), 5-Biphenyl-4-yl-3-hydroxy-2-[2-(1-oxo-4-phenyl-4a,8a-dihydrophthalazin-2(1H)-yl)ethyl]pentanoic acid (Compound No. 84), 5-Biphenyl-4-yl-3-hydroxy-2-[2-(3-oxo-2,3-dihydro-4H-1,4-benzoxazin-4-yl)ethyl]pentanoic acid (Compound No. 85), 5-Biphenyl-4-yl-2-{2-[(3aR,7aS)-1,3-dioxo-1,3,3a,4,7,7a-hexahydro-2H-isoindol-2-yl]ethyl}-3-hydroxypentanoic acid (Compound No. 86), 5-Biphenyl-4-yl-2-(2-{[(4-fluorophenyl)sulfonyl]amino}ethyl)-3-hydroxypentanoic acid (Compound No. 87), 5-Biphenyl-4-yl-2-(2-{[(3-fluorophenyl)acetyl] amino}ethyl)-3-hydroxypentanoic acid (Compound No. 88), 5-Biphenyl-4-yl-2-{2-[(4-fluorobenzoyl)amino]ethyl}-3-hydroxypentanoic acid (Compound No. 89), 5-Biphenyl-4-yl-3-hydroxy-2-[2-(5-methyl-1,3-dioxo-1,3-dihydro-2H-isoindol-2-yl)ethyl]pentanoic acid (Compound No. 90), 5-Biphenyl-4-yl-3-hydroxy-2-[2-(1-oxo-1,3-dihydro-2H-isoindol-2-yl)ethyl]pentanoic acid (Compound No. 91).

5-Biphenyl-4-yl-2-[2-({[(4-fluorophenyl)amino] carbonyl}amino)ethyl]-3-hydroxypentanoic acid (Compound No. 92), 5-Biphenyl-4-yl-2-[2-(4,4-dimethyl-2,6-dioxopiperidin-1-yl)ethyl]-3-hydroxypentanoic acid (Compound No. 93), 5-Biphenyl-4-yl-2-[2-(7,9-dioxo-8-azaspiro[4.5]dec-8-yl)ethyl]-3-hydroxypentanoic acid (Compound No. 94), 2-(3-Biphenyl-4-yl-1-hydroxypropyl)pent-4-ynoic acid (Compound No. 95), 5-Biphenyl-4-yl-3-hydroxy-2-[2-(2-oxo-1,3-benzoxazol-3 (2H)-yl)ethyl]pentanoic acid (Compound No. 96), 2-[2-(5-tert-Butyl-1,3-dioxo-1,3-dihydro-2H-isoindol-2-yl) ethyl]-3-hydroxy-5-[4-(6-methoxypyridin-3-yl)phenyl] pentanoic acid (Compound No. 97), 5-{4-[6-(Dimethylamino)pyridin-3-yl]phenyl}-2-[2-(1,3-dioxo-1,3-dihydro-2H-isoindol-2-yl)ethyl]-3-hydroxypentanoic acid (Compound No. 98), 2-[2-(1,3-Dioxo-1,3-dihydro-2H-isoindol-2-yl)ethyl]-3-hydroxy-5-[4'-(methylsulfonyl)biphenyl-4-yl]pentanoic acid (Compound No. 99), 5-[4'-(Aminocarbonyl)biphenyl-4-yl]-2-[2-(1,3-dioxo-1,3-dihydro-2H-isoindol-2-yl)ethyl]-3-hydroxypentanoic acid (Compound No. 100), 5-[4-(1-Benzyl-1H-pyrazol-4-yl)phenyl]-2-[2-(1,3-dioxo-1,3-dihydro-2H-isoindol-2-yl)ethyl]-3-hydroxypentanoic acid (Compound No. 101), 5-Biphenyl-4-yl-2-[2-(5,6-dichloro-1,3-dioxo-1,3-dihydro-2H-isoindol-2-yl)ethyl]-3-hydroxypentanoic acid (Compound No. 102), 5-Biphenyl-4-yl-2-[2-(2,4-dioxo-1,4-dihydroquinazolin-3 (2H)-yl)ethyl]-3-hydroxypentanoic acid (Compound No. 103), 5-Biphenyl-4-yl-2-[2-(1,3-dioxo-1,3-dihydro-2H-pyrrolo[3,4-c]pyridin-2-yl)ethyl]-3-hydroxypentanoic acid (Compound No. 104), 2-[2-(5-tert-Butyl-1,3-dioxo-1,3-dihydro-2H-isoindol-2-yl) ethyl]-5-(3',4'-difluorobiphenyl-4-yl)-3-hydroxypentanoic acid (Compound No. 105), (2R,3S+2S,3R)-2-[2-(5-tert-Butyl-1,3-dioxo-1,3-dihydro-2H-isoindol-2-yl)ethyl]-5-(4'-fluorobiphenyl-4-yl)-3-hydroxypentanoic acid (Compound No. 106), (2R,3S+2S,3R)-2-[2-(5-tert-Butyl-1,3-dioxo-1,3-dihydro-2H-isoindol-2-yl)ethyl]-3-hydroxy-5-[4'-(trifluoromethyl)biphenyl-4-yl]pentanoic acid (Compound No. 107), (2R,3R+2S,3S)-2-[2-(5-tert-Butyl-1,3-dioxo-1,3-dihydro-2H-isoindol-2-yl)ethyl]-5-(4'-fluorobiphenyl-4-yl)-3-hydroxypentanoic acid (Compound No. 108), (2R,3R+2S,3S)-2-[2-(5-tert-Butyl-1,3-dioxo-1,3-dihydro-2H-isoindol-2-yl)ethyl]-3-hydroxy-5-[4'-(trifluoromethyl)biphenyl-4-yl]pentanoic acid (Compound No. 109), 2-[2-(1,3-Dioxo-1,3-dihydro-2H-isoindol-2-yl)ethyl]-5-(3'-fluoro-4'-methoxybiphenyl-4-yl)-3-hydroxypentanoic acid (Compound No. 110), (2R,3S+2S,3R)-2-[2-(1,3-Dioxo-1,3-dihydro-2H-isoindol-2-yl)ethyl]-3-hydroxy-5-[4-(6-methylpyridin-3-yl)phenyl]pentanoic acid (Compound No. 111), (2R,3R+2S,3S)-2-[2-(1,3-Dioxo-1,3-dihydro-2H-isoindol-2-yl)ethyl]-3-hydroxy-5-[4-(6-methylpyridin-3-yl)phenyl]pentanoic acid (Compound No. 112), (2R,3R+2S,3S)-2-[2-(5-tert-Butyl-1,3-dioxo-1,3-dihydro-2H-isoindol-2-yl)ethyl]-3-hydroxy-5-(4'-methylbiphenyl-4-yl)pentanoic acid (Compound No. 113), (2R,3S+2S,3R)-2-[2-(5-tert-Butyl-1,3-dioxo-1,3-dihydro-2H-isoindol-2-yl)ethyl]-3-hydroxy-5-(4'-methylbiphenyl-4-yl)pentanoic acid (Compound No. 114), (2R,3R+2S,3S)-2-[2-(5-tert-Butyl-1,3-dioxo-1,3-dihydro-2H-isoindol-2-yl)ethyl]-3-hydroxy-5-(4'-methoxybiphenyl-4-yl)pentanoic acid (Compound No. 115), (2R,3R+2S,3S)-2-[2-(5-tert-Butyl-1,3-dioxo-1,3-dihydro-2H-isoindol-2-yl)ethyl]-5-(4'-chlorobiphenyl-4-yl)-3-hydroxypentanoic acid (Compound No. 116), (2R,3S+2S,3R)-2-[2-(5-tert-Butyl-1,3-dioxo-1,3-dihydro-2H-isoindol-2-yl)ethyl]-5-(4'-chlorobiphenyl-4-yl)-3-hydroxypentanoic acid (Compound No. 117), (2R,3S+2S,3R)-2-[2-(5-tert-Butyl-1,3-dioxo-1,3-dihydro-2H-isoindol-2-yl)ethyl]-3-hydroxy-5-(4'-methoxybiphenyl-4-yl)pentanoic acid (Compound No. 118), 2-[2-(1,3-Dioxo-1,3-dihydro-2H-isoindol-2-yl)ethyl]-3-hydroxy-5-(4-pyrimidin-5-ylphenyl)pentanoic acid (Compound No. 119), 5-Biphenyl-4-yl-3-hydroxy-2-[2-(7-methyl-4-oxo-1,2,3-benzotriazin-3(4H)-yl)ethyl]pentanoic acid (Compound No. 120), 5-Biphenyl-4-yl-2-[2-(5-tert-butyl-1,3-dioxo-1,3-dihydro-2H-isoindol-2-yl)ethyl]-3-hydroxypentanoic acid (Compound No. 121), (2R,3S)-5-Biphenyl-4-yl-3-hydroxy-2-[2-(1H-indol-3-yl) ethyl]pentanoic acid (Compound No. 122), (2R,3R)-5-Biphenyl-4-yl-3-hydroxy-2-[2-(1H-indol-3-yl) ethyl]pentanoic acid (Compound No. 123), 5-Biphenyl-4-yl-3-hydroxy-2-[2-(1-oxo-1,3-dihydro-2H-isoindol-2-yl)butyl]pentanoic acid (Compound No. 124), (2R,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 125), (2S,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 126), (2R,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 127), (2S,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 128), (2R,3S)-2-[2-(1,3-Dioxo-1,3-dihydro-2H-isoindol-2-yl) ethyl]-3-hydroxy-5-[4-(6-methoxypyridin-3-yl)phenyl] pentanoic acid (Compound No. 129), (2S,3R)-2-[2-(1,3-Dioxo-1,3-dihydro-2H-isoindol-2-yl) ethyl]-3-hydroxy-5-[4-(6-methoxypyridin-3-yl)phenyl] pentanoic acid (Compound No. 130), (2R,3R)-2-[2-(1,3-Dioxo-1,3-dihydro-2H-isoindol-2-yl) ethyl]-3-hydroxy-5-[4-(6-methoxypyridin-3-yl)phenyl] pentanoic acid (Compound No. 131), (2S,3S)-2-[2-(1,3-Dioxo-1,3-dihydro-2H-isoindol-2-yl) ethyl]-3-hydroxy-5-[4-(6-methoxypyridin-3-yl)phenyl] pentanoic acid (Compound No. 132), (2R,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 133), (2S,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 134), (2R,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 135), and (2S,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 136).

In another embodiment, the invention encompasses separation of the individual enantiomers or diastereomer pairs or single diastereomers. A person ordinarily skilled in the art of this invention may optionally choose one or more ways to obtain chirally pure compounds. The present invention includes separation of a representative set of compounds either as diastereomeric pairs or single diastereomers by preparative thin layer chromatography and/or by HPLC, using an achiral or chiral column as required.

In yet another embodiment, the present invention relates to the therapeutically effective dose of a compound of Formula I in combination with one or more of other therapeutic agents used for treating various inflammatory and allergic diseases. Examples of such therapeutic agents include, but are not limited to, 1) anti-inflammatory agents, experimental or commercial (i) such as nonsteroidal anti-inflammatory agents piroxicam, diclofenac, propionic acids, fenamates, pyrazolones, salicylates, PDE-4/p38 MAP Kinase/Cathepsin inhibitors, (ii) leukotrienes LTC4/LTD4/LTE4/LTB4-Inhibitors, 5-lipoxygenase inhibitors and PAF-receptor antagonists, (iii) Cox-2 inhibitors, (iv) MMP inhibitors, and (v) interleukin-I inhibitors;

2) antihypertensive agents, (i) ACE inhibitors, e.g., enalapril, lisinopril, valsartan, telmisartan and quinapril, (ii) angiotensin II receptor antagonists and agonists, e.g., losartan, candesartan, irbesartan, valsartan, and eprosartan, (iii) β-blockers, and (iv) calcium channel blockers;

3) immunosuppressive agents such as cyclosporine, azathioprine and methotrexate, and anti-inflammatory corticosteroids.

The following definitions apply to terms as used herein.

The term "alkyl," unless otherwise specified, refers to a monoradical branched or unbranched saturated hydrocarbon chain having from 1 to 20 carbon atoms. This term can be exemplified by groups such as methyl, ethyl, n-propyl, isopropyl, n-butyl, iso-butyl, sec-butyl, t-butyl, n-pentyl, isopentyl, neopentyl, n-hexyl, n-decyl, tetradecyl, and the like. Alkyl groups may be substituted further with one or more substituents selected from alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, aryl, heterocyclyl, heteroaryl, arylthio, thiol, alkylthio, aryloxy, nitro, aminosulfonyl, COOH, aminocarbonylamino, —NHC(=O)R$_f$, —NR$_f$R$_q$, —C(=O)NR$_f$R$_q$, —NHC(=O)NR$_f$R$_q$, —C(=O)heteroaryl, C(=O)heterocyclyl, —O—C(=O)NR$_f$R$_q$ {wherein R$_f$ and R$_q$ are independently selected from alkyl, alkenyl, cycloalkyl, cycloalkenyl, aryl, aralkyl, heterocyclyl, heteroaryl, heterocyclylalkyl, heteroarylalkyl}, nitro, or —SO$_2$R$_6$ (wherein R$_6$ is alkyl, alkenyl, alkynyl, cycloalkyl, aralkyl, aryl, heterocyclyl, heteroaryl, heteroarylalkyl or heterocyclylalkyl). Unless otherwise constrained by the definition, alkyl substituents may be further substituted by 1-3 substituents selected from alkyl, carboxy, —NR$_f$R$_q$, —C(=O)NR$_f$R$_q$, —OC(=O) NR$_f$R$_q$, —NHC(=O)NR$_f$R$_q$ (wherein R$_f$ and R$_q$ are the same as defined earlier), hydroxy, alkoxy, halogen, CF$_3$, cyano, and —SO$_2$R$_6$, (wherein R$_6$ are the same as defined earlier); or an alkyl group also may be interrupted by 1-5 atoms of groups independently selected from oxygen, sulfur or —NR$_a$— {wherein R$_a$ is selected from hydrogen, alkyl, cycloalkyl, alkenyl, cycloalkenyl, alkynyl, aryl, acyl, aralkyl, —C(=O)OR$_f$ (wherein R$_f$ is the same as defined earlier), SO$_2$R$_6$ (where R$_6$ is as defined earlier), or —C(=O)NR$_f$R$_q$ (wherein R$_f$ and R$_q$ are as defined earlier)}. Unless otherwise constrained by the definition, all substituents may be substituted further by 1-3 substituents selected from alkyl, carboxy, —NR$_f$R$_q$, —C(=O)NR$_f$R$_q$, —O—C(=O)NR$_f$R$_q$ (wherein R$_f$ and R$_q$ are the same as defined earlier) hydroxy, alkoxy, halogen, CF$_3$, cyano, and —SO$_2$R$_6$ (where R$_6$ is same as defined earlier); or an alkyl group as defined above that has both substituents as defined above and is also interrupted by 1-5 atoms or groups as defined above.

The term "alkenyl," unless otherwise specified, refers to a monoradical of a branched or unbranched unsaturated hydrocarbon group having from 2 to 20 carbon atoms with cis, trans, or geminal geometry. In the event that alkenyl is attached to a heteroatom, the double bond cannot be alpha to the heteroatom. Alkenyl groups may be substituted further with one or more substituents selected from alkyl, alkynyl, alkoxy, cycloalkyl, cycloalkenyl, acyl, acylamino, acyloxy, —NHC(=O)R$_f$, —NR$_f$R$_q$, —C(=O)NR$_f$R$_q$, —NHC(=O)NR$_f$R$_q$, —O—C(=O)NR$_f$R$_q$ (wherein R$_f$ and R$_q$ are the same as defined earlier), alkoxycarbonylamino, azido, cyano, halogen, hydroxy, oxo, thiocarbonyl, carboxy, arylthio, thiol, alkylthio, aryl, aralkyl, aryloxy, heterocyclyl, heteroaryl, heterocyclyl alkyl, heteroaryl alkyl, aminosulfonyl, aminocarbonylamino, alkoxyamino, nitro, or SO$_2$R$_6$ (wherein R$_6$ are is same as defined earlier). Unless otherwise constrained by the definition, alkenyl substituents optionally may be substituted further by 1-3 substituents selected from alkyl, carboxy, hydroxy, alkoxy, halogen, —CF$_3$, cyano, —NR$_f$R$_q$, —C(=O)NR$_f$R$_q$, —O—C(=O)NR$_f$R$_q$ (wherein R$_f$ and R$_q$ are the same as defined earlier) and —SO$_2$R$_6$ (where R$_6$ is same as defined earlier).

The term "alkynyl," unless otherwise specified, refers to a monoradical of an unsaturated hydrocarbon, having from 2 to 20 carbon atoms. In the event that alkynyl is attached to a heteroatom, the triple bond cannot be alpha to the heteroatom. Alkynyl groups may be substituted further with one or more substituents selected from alkyl, alkenyl, alkoxy, cycloalkyl, cycloalkenyl, acyl, acylamino, acyloxy, alkoxycarbonylamino, azido, cyano, halogen, hydroxy, oxo, thiocarbonyl, carboxy, arylthio, thiol, alkylthio, aryl, aralkyl, aryloxy, aminosulfonyl, aminocarbonylamino, nitro, heterocyclyl, heteroaryl, heterocyclylalkyl, heteroarylalkyl, —NHC(=O)R$_f$, —NR$_f$R$_q$, —NHC(=O)NR$_f$R$_q$, —C(=O)NR$_f$R$_q$, —O—C(=O)NR$_f$R$_q$ (wherein R$_f$ and R$_q$ are the same as defined earlier), or —SO$_2$R$_6$ (wherein R$_6$ is as defined earlier). Unless otherwise constrained by the definition, alkynyl substituents optionally may be substituted further by 1-3 substituents selected from alkyl, carboxy, carboxyalkyl, hydroxy, alkoxy, halogen, CF$_3$, —NR$_f$R$_q$, —C(=O)NR$_f$R$_q$, —NHC(=O)NR$_f$R$_q$, —C(=O)NR$_f$R$_q$ (wherein R$_f$ and R$_q$ are the same as defined earlier), cyano, or —SO$_2$R$_6$ (where R$_6$ is same as defined earlier).

The term "aralkyl," unless otherwise specified, refers to alkyl-aryl linked through an alkyl portion (wherein alkyl is as defined above) and the alkyl portion contains 1-6 carbon atoms and aryl is as defined below. Examples of aralkyl groups include benzyl, ethylphenyl and the like.

The term "aryl," unless otherwise specified, refers to carbocyclic aromatic groups, for example, phenyl, biphenyl or napthyl ring and the like, optionally substituted with 1 to 3 substituents selected from halogen (e.g., F, Cl, Br, I), hydroxy, alkyl, alkenyl, alkynyl, cycloalkyl, alkoxy, acyl, aryloxy, CF$_3$, cyano, nitro, COOR$_e$ (wherein R$_e$ is hydrogen, alkyl, alkenyl, cycloalkyl, aralkyl, heterocyclylalkyl, heteroarylalkyl), NHC (=O)R$_f$, —NR$_f$R$_q$, —C(=O)NR$_f$R$_q$, —NHC(=O)NR$_f$R$_q$, —O—C(=O)NR$_f$R$_q$ (wherein R$_f$ and R$_q$ are the same as defined earlier), —SO$_2$R$_6$ (wherein R$_6$ is same as defined earlier), carboxy, heterocyclyl, heteroaryl, heterocyclylalkyl, heteroarylalkyl or amino carbonyl amino. The aryl group optionally may be fused with a cycloalkyl group, wherein the cycloalkyl group may optionally contain heteroatoms selected from O, N or S.

The term "aryloxy" denotes the group O-aryl, wherein aryl is as defined above.

The term "heteroaryl," unless otherwise specified, refers to an aromatic ring structure containing 5 or 6 ring atoms, or a bicyclic aromatic group having from 8 to 10 ring atoms, with one or more heteroatom(s) independently selected from N, O or S optionally substituted with 1 to 4 substituent(s) selected from halogen (e.g., F, Cl, Br, I), hydroxy, alkyl, alkenyl, alkynyl, cycloalkyl, acyl, carboxy, aryl, alkoxy, aralkyl, cyano, nitro, heterocyclyl, heteroaryl, —NR$_f$R$_q$, CH=NOH, —(CH$_2$)$_w$C(=O)R$_g$ {wherein w is an integer from 0-4 and R$_g$ is hydrogen, hydroxy, OR$_f$, NR$_f$R$_q$, —NHOR$_z$ or —NHOH}, —C(=O)NR$_f$R$_q$ and —NHC(=O)NR$_f$R$_q$, —SO$_2$R$_6$, —O—C(=O)NR$_f$R$_q$, —O—C(=O)R$_f$, —O—C(=O)OR$_f$ (wherein R$_6$, R$_f$ and R$_q$ are as defined earlier, and R$_z$ is alkyl, cycloalkyl, aryl, heteroaryl, heterocyclyl, heteroarylalkyl or heterocyclylalkyl). Unless otherwise constrained by the definition, the substituents are attached to a ring atom, i.e., carbon or heteroatom in the ring. Examples of heteroaryl groups include oxazolyl, imidazolyl, pyrrolyl, 1,2,3-triazolyl, 1,2,4-triazolyl, tetrazolyl, thiazolyl, oxadiazolyl, benzoimidazolyl, thiadiazolyl, pyridinyl, pyridazinyl, pyrimidinyl, pyrazinyl, thienyl, isoxazolyl, triazinyl, furanyl, benzofuranyl, indolyl, benzothiazolyl, or benzoxazolyl, and the like.

The term 'heterocyclyl," unless otherwise specified, refers to a non-aromatic monocyclic or bicyclic cycloalkyl group having 5 to 10 atoms wherein 1 to 4 carbon atoms in a ring are replaced by heteroatoms selected from O, S or N, and optionally are benzofused or fused heteroaryl having 5-6 ring members and/or optionally are substituted, wherein the substituents are selected from halogen (e.g., F, Cl, Br, I), hydroxy, alkyl, alkenyl, alkynyl, cycloalkyl, acyl, aryl, alkoxy, alkaryl, cyano, nitro, oxo, carboxy, heterocyclyl, heteroaryl, —O—C(=O)R$_f$, —O—C(=O)OR$_f$, —C(=O)NR$_f$R$_q$, SO$_2$R$_6$, —O—C(=O)NR$_f$R$_q$, —NHC(=O)NR$_f$R$_q$, —NR$_f$R$_q$ (wherein R$_6$, R$_f$ and R$_q$ are as defined earlier) or guanidine. Heterocyclyl can optionally include rings having one or more double bonds. Unless otherwise constrained by the definition, the substituents are attached to the ring atom, i.e., carbon or heteroatom in the ring. Also, unless otherwise constrained by the definition, the heterocyclyl ring optionally may contain one or more olefinic bond(s). Examples of heterocyclyl groups include oxazolidinyl, tetrahydrofuranyl, dihydrofuranyl, dihydropyridinyl, dihydroisoxazolyl, dihydrobenzofuryl, azabicyclohexyl, dihydroindolyl, pyridinyl, isoindole 1,3-dione, piperidinyl or piperazinyl.

The term "cycloalkyl," unless otherwise specified, refers to cyclic alkyl groups of from 3 to 20 carbon atoms having a single cyclic ring or multiple condensed rings, which may optionally contain one or more olefinic bonds, unless otherwise constrained by the definition. Such cycloalkyl groups can include, for example, single ring structures, including cyclopropyl, cyclobutyl, cyclooctyl, cyclopentenyl, and the like, or multiple ring structures, including adamantanyl, and bicyclo [2.2.1]heptane, or cyclic alkyl groups to which is fused an aryl group, for example, indane, and the like. Spiro and fused ring structures can also be included. Cycloalkyl groups may be substituted further with one or more substituents selected from alkyl, alkenyl, alkynyl, alkoxy, cycloalkyl, cycloalkenyl, acyl, acylamino, acyloxy, alkoxycarbonylamino, azido, cyano, halogen, hydroxy, oxo, thiocarbonyl, carboxy, carboxyalkyl, arylthio, thiol, alkylthio, aryl, aralkyl, aryloxy, aminosulfonyl, aminocarbonylamino, —NR$_f$R$_q$, —NHC(=O)NR$_f$R$_q$, —NHC(=O)R$_f$, —C(=O)NR$_f$R$_q$, —O—C(=O)NR$_f$R$_q$ (wherein R$_f$ and R$_q$ are the same as defined earlier), nitro, heterocyclyl, heteroaryl, heterocyclylalkyl, heteroarylalkyl, or SO$_2$—R$_6$ (wherein R$_6$ is same as defined earlier). Unless otherwise constrained by the definition, cycloalkyl substituents optionally may be substituted further by 1-3 substituents selected from alkyl, carboxy, hydroxy, alkoxy, halogen, CF$_3$, —NR$_f$R$_q$, —C(=O)NR$_f$R$_q$, —NHC(=O)NR$_f$R$_q$, —OC(=O)NR$_f$R$_q$ (wherein R$_f$ and R$_q$ are the same as defined earlier), cyano or —SO$_2$R$_6$ (where R$_6$ is same as defined earlier). "Cycloalkylalkyl" refers to alkyl-cycloalkyl group linked through alkyl portion, wherein the alkyl and cycloalkyl are the same as defined earlier.

The term "cycloalkylalkyl" refers to cycloalkyl group linked through alkyl portion, wherein the alkyl having 1 to 6 carbon atoms and cycloalkyl are the same as defined earlier.

"Heteroarylalkyl" refers to alkyl-heteroaryl group linked through alkyl portion, wherein the alkyl and heteroaryl are as defined earlier.

"Heterocyclylalkyl" refers to alkyl-heterocyclyl group linked through alkyl portion, wherein the alkyl and heterocyclyl are as defined earlier.

"Amine," unless otherwise specified, refers to —NH$_2$. "Substituted amino" unless otherwise specified, refers to a group —N(R$_k$)$_2$ wherein each R$_k$ is independently selected from the group hydrogen provided that both R$_k$ groups are not hydrogen (defined as "amino"), alkyl, alkenyl, alkynyl, aralkyl, cycloalkyl, aryl, heteroaryl, heterocyclyl, heterocyclylalkyl, heteroarylalkyl, acyl, S(O)$_m$R$_6$ (wherein m and R$_6$ is the same as defined above), —C(=R$_v$)NR$_x$R$_y$ (wherein R$_v$ is O or S & R$_x$ and R$_y$ are the same as defined earlier) or NHC(=R$_v$)NR$_y$R$_x$ (wherein R$_v$, R$_y$ and R$_x$ are the same as defined earlier). Unless otherwise constrained by the definition, all amino substituents may optionally be further substituted by 1-3 substituents chosen from alkyl, aralkyl, cycloalkyl, aryl, heteroaryl, heterocyclyl, carboxy, —COOR$_7$ (wherein R$_7$ is the same as defined earlier), hydroxy, alkoxy, halogen, CF$_3$, cyano, —C(=R$_v$)NR$_x$R$_y$ (wherein R$_v$ is the same as defined earlier), —O(C=O)NR$_x$R$_y$, —OC(=R$_v$)NR$_x$R$_y$ (wherein R$_v$, R$_y$ and R$_v$ are the same as defined earlier), —S(O)$_m$R$_6$ (where R$_6$ and m is the same as defined above).

"Acyl" refers to —C(=O)R" wherein R" is selected from hydrogen, alkyl, cycloalkyl, aryl, aralkyl, heteroaryl, heterocyclyl, heteroarylalkyl or heterocyclylalkyl.

The term "thioacyl" refers to —C(=S)R$_4$ wherein R$_4$ is the same as defined above. "Thiocarbonyl" refers to —C(=S)H. "Substituted thiocarbonyl" refers to —C(=S)R", wherein R" is selected from alkyl, cycloalkyl, aryl, aralkyl, heteroaryl, heterocyclyl, heteroarylalkyl or heterocyclylalkyl, amine or substituted amine.

The term "halogen" refers to fluorine, chlorine, bromine or iodine;

The term "leaving group" refers to groups that exhibit or potentially exhibit the properties of being labile under the synthetic conditions and also, of being readily separated from synthetic products under defined conditions. Examples of leaving groups include, but are not limited to, halogen (e.g., F, Cl, Br, I), triflates, tosylate, mesylates, alkoxy, thioalkoxy, or hydroxy radicals and the like.

The term "protecting groups" refers to moieties that prevent chemical reaction at a location of a molecule intended to be left unaffected during chemical modification of such molecule. Unless otherwise specified, protecting groups may be used on groups, such as hydroxy, amino, or carboxy. Examples of protecting groups are found in T. W. Greene and P. G. M. Wuts, "Protective Groups in Organic Synthesis", 2$^{nd}$ Ed., John Wiley and Sons, New York, N.Y., which is incorporated herein by reference. The species of the carboxylic protecting groups, amino protecting groups or hydroxy protecting groups employed are not critical, as long as the derivatised moieties/moiety is/are stable to conditions of subsequent reactions and can be removed without disrupting the remainder of the molecule.

The compounds of this invention can contain one or more asymmetric carbon atoms and thus may occur as racemic mixtures, enantiomers and diastereomers. These compounds can also exist as conformers/rotamers. All such isomeric forms of these compounds are included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are envisioned as part of the invention.

The term "pharmaceutically acceptable salts" forming part of this invention includes the salts of carboxylic acid moiety, which may be prepared by reacting the compound with appropriate base to provide corresponding base addition salts. Examples of such bases are alkali metal hydroxide including potassium hydroxide, sodium hydroxide and lithium hydroxide; alkaline earth metal hydroxides such as magnesium hydroxide and calcium hydroxide. Further the salts of organic bases such as lysine, arginine, guanidine, ethanolamine, choline and the like; inorganic bases e.g., ammonium or substituted ammonium salts are also included. Wherever appropriate, compounds of the present invention may also form the acid addition salts by treating the said compounds with pharmaceutically acceptable organic and inorganic acids, e.g., hydrohalides such as hydrochloride, hydrobromide, hydroiodide; other mineral acids and their corresponding salts such as sulphate, nitrate, phosphate etc.; and alkyl and mono-arylsulphonates such as ethane sulphonate, toluene sulphonate and benzene sulphonate; and other organic acids and their corresponding salts such as acetate, tartarate, maleate, succinate, citrate etc.

DETAILED DESCRIPTION OF THE INVENTION

Compounds of the present invention may be prepared by techniques well known in the organic synthesis and familiar to a practitioner ordinarily skilled in art of this invention. In addition, the process described herein may prepare the compounds of the present invention, however that may not be the only means by which the compounds described may be synthesised. Further, the various synthetic steps described herein may be performed in an alternate sequence in order to give the desired compounds.

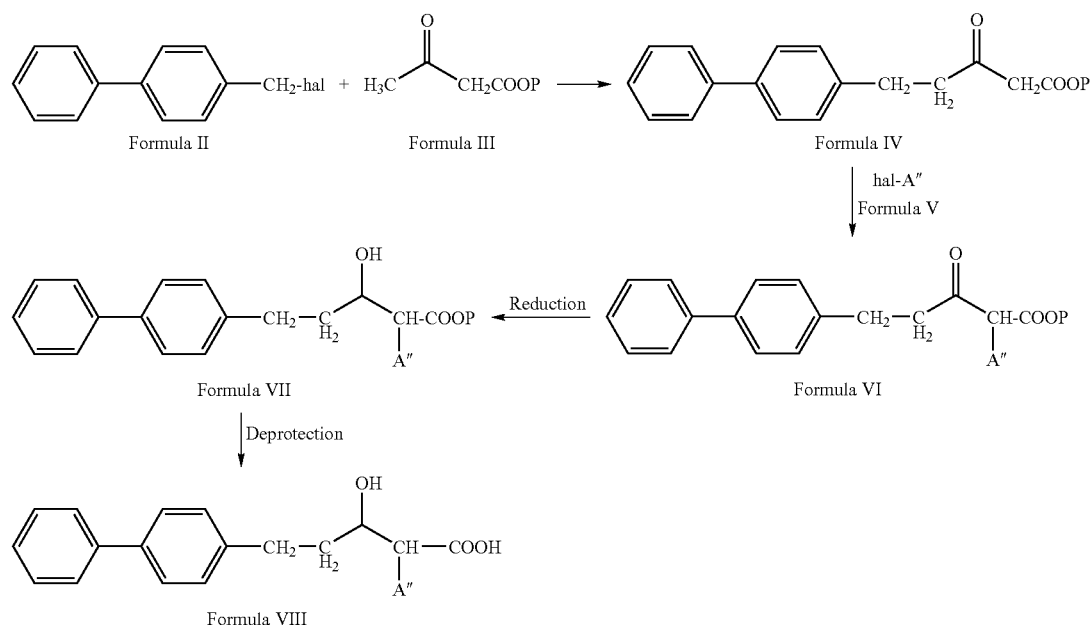

Compounds of Formula VIII can be prepared by, for example, following the synthetic route as depicted in Scheme I. Thus a compound of Formula II (wherein hal is Cl, Br or I) can be reacted with a compound of Formula III [wherein P is alkyl (for example, tert-butyl, ethyl or methyl) or aralkyl (or example, benzyl)] to give a compound Formula IV, which on reaction with a compound of Formula V (wherein hal is the same as defined above and A" is aralkyl, heterocyclylalkyl, heteroarylalkyl or cycloalkylalkyl) can form a compound of Formula VI. A compound of Formula VI on reduction can form a compound of Formula VII, which on deprotection can yield a compound of Formula VIII.

The reaction of a compound of Formula II with a compound of Formula III to give a compound of Formula IV can be carried out in the presence of a base or a combination thereof, for example, sodium hydride, butyl lithium or lithium diisopropylamide in an organic solvent, for example, tetrahydrofuran, dimethylformamide, dioxane or diethylether.

The reaction of a compound of Formula IV with a compound of Formula V to give a compound of Formula VI can be carried out in the presence of a base for example, potassium tert-butoxide, sodium (m)ethoxide, sodium hydride, lithium diisopropylamide, butyl lithium or lithium/sodium/potassium hexamethyldisilazide, optionally in the presence of a catalyst, for example, tetrabutylammonium iodide or tetrabutylammonium bromide, in an appropriate organic solvent for example, t-butanol, ethanol, tetrahydrofuran, dimethylformamide, diethylether or dioxane.

The compound of Formula VI undergoes reduction to give a compound of Formula VII in the presence of reducing agent, for example, sodium borohydride or lithium borohydride in organic solvent, for example, methanol, ethanol, propanol, isopropylalcohol and/or tetrahydrofuran.

The hydrolysis of a compound of Formula VII to give a compound of Formula VIII, when P is t-butyl can be carried out with acids, for example, trifluoroacetic acid or hydrochloric acid, in an organic solvent or a solvent system including, for example, dichloromethane, dichloroethane, THF or dioxane in water.

A compound of Formula XXI can be prepared, for example, by following the synthetic route as depicted, for example, in Scheme II. Thus a compound of Formula IX (wherein hal is the same as defined earlier) on reaction with a compound of Formula III (wherein P is the same as defined earlier) can give a compound of Formula X, which can be reacted with a compound of Formula XI (wherein hal and n are the same as defined earlier and $P_1$ is silyl protecting group for example, tert-butyldimethylsilane, tert-butyldiphenlsilane or triisopropylsilane to give a compound of Formula XII, which can undergo reduction to give a compound of Formula XIII. The compound of Formula XIII on reaction with a compound of Formula XIV [wherein $P_2$ is aralkyl (for example, benzyl, 4-methoxybenzyl or 2,4,6-trimethoxybenzyl) or heterocyclyl (for example, tetrahydropyranyl)] can

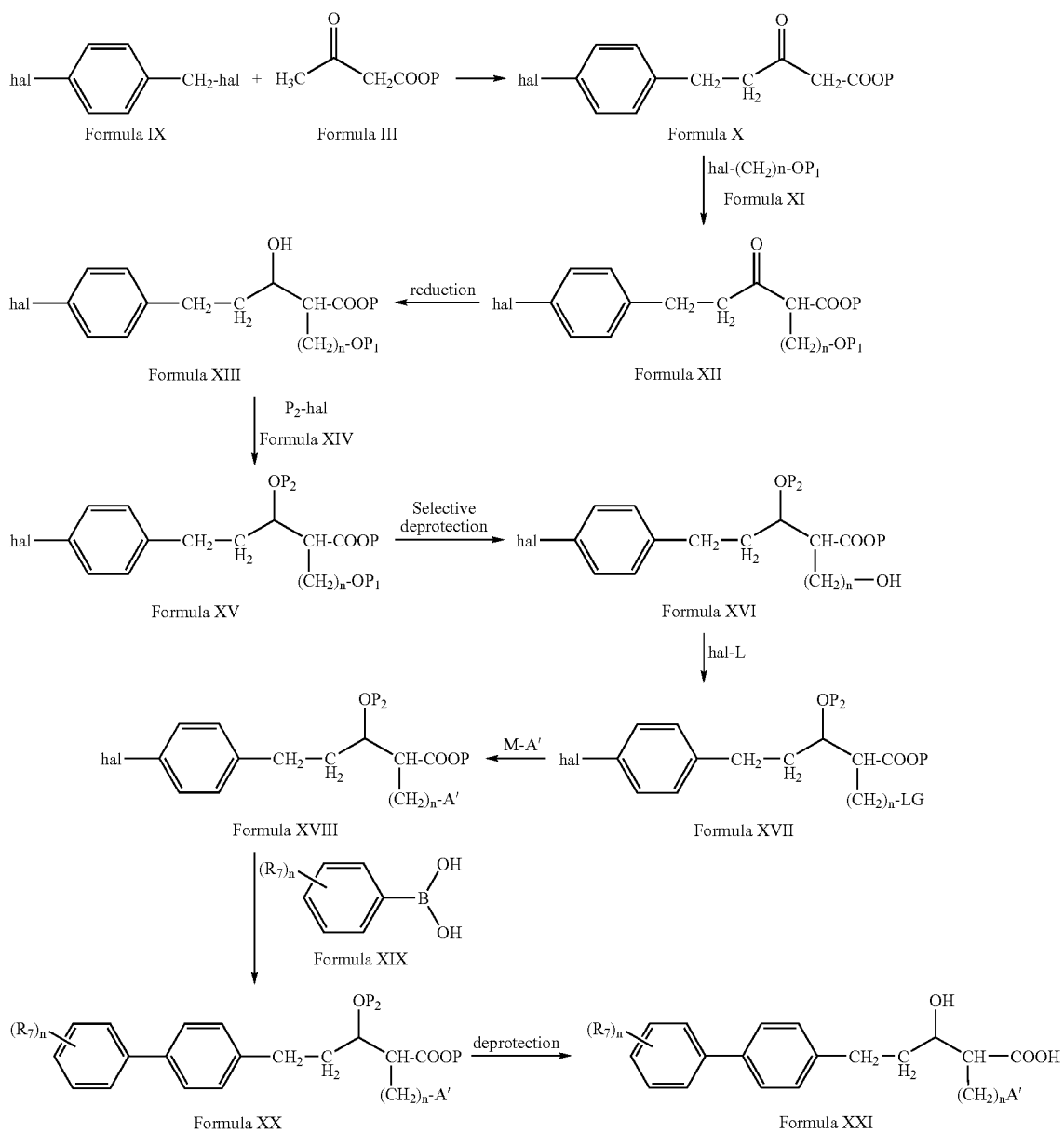

form a compound of Formula XV, which can undergo selective deprotection to form a compound of Formula XVI, which can then be converted to a compound of Formula XVII (wherein LG is a leaving group such as mesyl, tosyl or triflyl or a halide (hal) as defined earlier) by reaction either with a compound of Formula L-hal (wherein L is methanesulphonyl, p-toluenesulphonyl and hal is the same as defined earlier), by reaction with triflic anhydride or by reaction with triphenylphosphine and a halide source such as carbon tetrabromide or iodine. A compound of Formula XVII can be reacted with a compound of Formula M-A' (wherein A' is aryl, heteroaryl, heterocyclyl or cycloalkyl and M is metal for example, potassium, lithium or sodium) or by reaction of A' in the presence of a base to yield a compound of Formula XVIII. The compound of Formula XVIII can be reacted with a compound of Formula XIX (wherein n is an integer from 1 to 5 and $R_7$ is hydrogen, halogen (F, Cl, Br, I), hydroxy, —COOH, —COOR$_4$ (wherein $R_4$ is the same as defined earlier), alkyl, alkenyl, alkynyl, cycloalkyl, alkoxy, alkenyloxy, alkynyloxy, aryloxy, heterocyclyloxy, heteroaryloxy, cycloalkyloxy, acyl, thioacyl, cyano, nitro, amino, —CHO, —OCF$_3$, —CF$_3$, —SCF$_3$, —NR$_4$R$_5$, —C(=Y)NR$_4$R$_5$, —NHC(=Y)R$_4$, —NHC(=Y)NR$_5$R$_x$, —NHC(=O)OR$_4$, —NHSO$_2$R$_4$, (SO)$_m$R$_4$ (wherein R$_4$, R$_5$, Rx, Y and m are the same as defined earlier), aryl, heterocyclyl, heteroaryl, heterocyclylalkyl or heteroarylalkyl which may optionally be substituted further) to form a compound of Formula XX, which can be deprotected to form a compound of Formula XXI.

The reaction of a compound of Formula IX with a compound of Formula III to give a compound of Formula X can be carried out similarly to the reaction of a compound of Formula II and a compound of Formula III to yield a compound of Formula IV.

The reaction of a compound of Formula X with a compound of Formula XI to give a compound of Formula XII can be carried out similarly to the reaction of a compound of Formula IV with a compound of Formula V to give a compound of Formula VI.

The reduction of a compound of Formula XII to give a compound of Formula XIII can be carried out similarly to the reduction of a compound of Formula VI to give a compound of Formula VII.

The reaction of a compound of Formula XIII with a compound of Formula XIV to give a compound of Formula XV can be carried out in the presence of Lewis acid, for example, boron trifluoride, triflic acid, camphor sulphonic acid, pyridinium p-toulenesulphonate or trityl perchlorate, in an organic solvent, for example, tetrahydrofuran, dimethylformamide, diethyl ether or dioxane.

The selective deprotection of a compound of Formula XV to give a compound of Formula XVI can be carried out with deprotecting agents, for example, tetrabutylammonium fluoride or potassium fluoride, in an organic solvent, for example, tetrahydrofuran, dimethylformamide, diethyl ether or dioxane.

A compound of Formula XVI can be reacted with a compound of Formula L-hal, triflic anhydride or by reaction with triphenylphosphine and a halide source such as carbon tetrabromide or iodine to give a compound of Formula XVII, optionally in the presence of a base, for example, triethylamine, pyridine, N-methylmorpholine or diisopropylethylamine, in an organic solvent, for example, dichloromethane, dichloroethane, or tetrahydrofuran.

The reaction of a compound of Formula XVII with a compound of Formula M-A' to yield a compound of Formula XVIII can be carried out in an organic solvent, for example, tetrahydrofuran, dimethyl sulphoxide, dimethylformamide, acetonitrile, dioxane, dimethylacetamide. Alternately, the reaction of a compound of Formula XVII with a compound of Formula A' to yield a compound of Formula XVIII can be carried out in the presence of a base, for example, sodium hydride, potassium tert-butoxide, sodium (m)ethoxide, in an organic solvent, for example, tetrahydrofuran, dimethyl sulphoxide, dimethylformamide, acetonitrile, dioxane, dimethylacetamide.

The reaction of a compound of Formula XVIII with a compound of Formula XIX can be carried out in the presence of a metal catalyst such as tetrakis(triphenylphosphine) palladium (0), tetrakis(tricyclohexylphosphine) palladium (0), tetrakis(tri-tert-butylphosphine) palladium (0) or palladium acetate and triphenylphosphine, in the presence of a base, such as potassium carbonate ot cesium carbonate, in an organic solvent, such as toluene, dimethyl sulphoxide, dimethylformamide, tetrahydrofuran, dioxane or diethyl ether.

The deprotection of a compound of Formula XX to give a compound of Formula XXI can be carried out similarly as that of a compound of Formula VII to give a compound of Formula VIII.

Scheme III

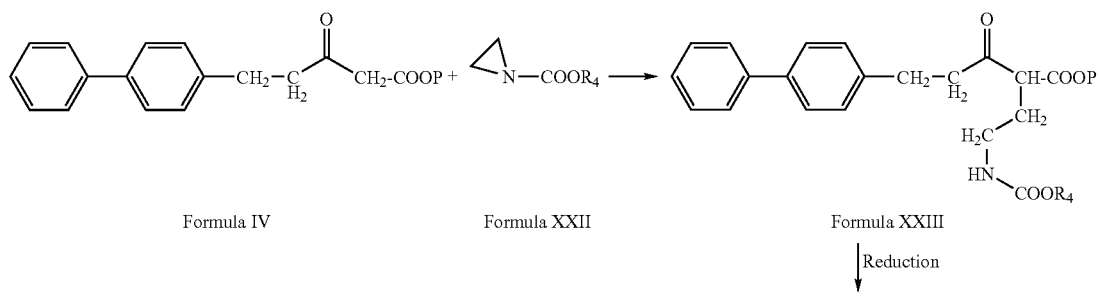

Formula IV   Formula XXII   Formula XXIII

Reduction

-continued

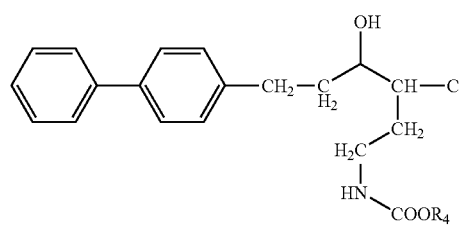

Formula XXV

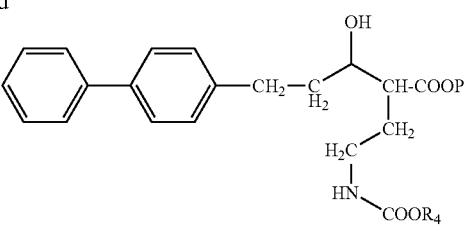

Formula XXIV

Path b | Rt-COOH
Formula XXVI

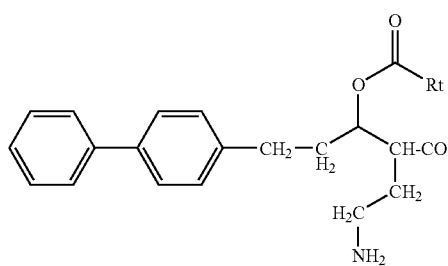

Formula XXVIII

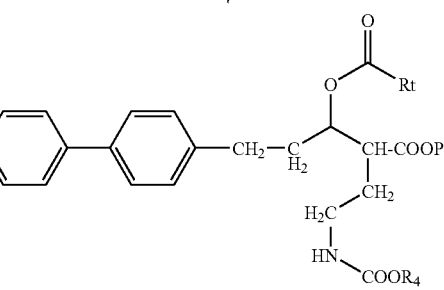

Formula XXVII

RD
N-derivatization ↓

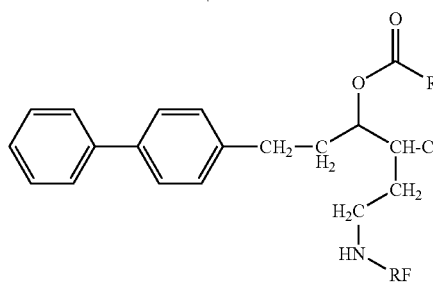

Formula XXIX deprotection →

Formula XXX deprotection ↓

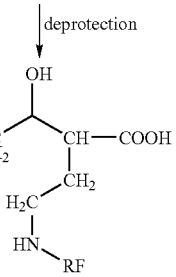

Formula XXXI

A compound of Formulae XXV and XXXI can be prepared, for example, by following the synthetic route as depicted, for example, in Scheme III. Thus a compound of Formula IV (wherein P is the same as defined earlier) can be reacted with a compound of Formula XXII (wherein $R_4$ is the same as defined earlier) to give a compound of Formula XXIII, Path a: which on reduction can give a compound of Formula XXIV, which can be further deprotected to yield a compound of Formula XXV, or Path b: which on reaction with a compound of Formula XXVI (wherein Rt is alkyl, aryl, cycloalkyl, aralkyl, heterocyclylalkyl or heteroarylalkyl) gives a compound of Formula XXVII, which can undergo deprotection to give a compound of Formula XXVIII, which can undergo N-derivatization with a compound of Formula RD (wherein RD is $R_4COhal$, $halCOOR_4$, $R_4SO_2hal$ or $(R_4)N=C(=Y)$ wherein Y is O or S) to give a compound of Formula XXIX (wherein $R_f$ is $R_4CO—$, $R_4SO_2—$, $R_4OCO—$ or $(R_4)NH—C(=Y)—$), which can undergo deprotection to give a compound of Formula XXX, which can undergo further deprotection to give a compound of Formula XXXI.

The reaction of a compound of Formula IV with a compound of Formula XXII to give a compound of Formula XXIII can be carried out in the presence of a base, for example, potassium tert-butoxide, sodium hydride, sodium (m)ethoxide, lithium diisopropylamide, and/or butyl lithium, in an organic solvent, for example, tetrahydrofuran, dimethylformamide, diethyl ether or dioxane.

The reduction of a compound of Formula XXIII to give a compound of Formula XXIV can be carried out similarly to the reduction of a compound of Formula VI to give a compound of Formula VII.

The deprotection of a compound of Formula XXIV (path a) to give a compound of Formula XXV can be carried out similarly as that of a compound of Formula VII to give a compound of Formula VIII.

The reaction of a compound of Formula XXIV (path b) with a compound of Formula XXVI to give a compound of Formula XXVII can be carried out using coupling agents, such as EDCI or DCC, in the presence of base, such as dimethylaminopyridine, N-methylmorpholine or diisopropylethylamine, in an organic solvent, such as dichloromethane, dichloroethane, chloroform and carbon tetrachloride.

The deprotection of a compound of Formula XXVII to give a compound of Formula XXVIII can be carried out in the presence of a deprotecting agent, for example, palladium on carbon in presence of hydrogen gas, or palladium on carbon with a source of hydrogen gas, for example, ammonium formate, cyclohexene or formic acid.

The N-derivatization of a compound of Formula XXVIII with a compound of Formula RD (wherein RD is $R_4COhal$ or $halCOOR_4$) to give a compound of Formula XXIX (wherein RF is $R_4CO—$, $R_4OCO—$) can be carried out in the presence of a base, for example, pyridine, N-methylmorpholine, N-ethyldiisopropylamine, triethylamine or potassium carbonate.

The N-derivatization of a compound of Formula XXVIII with a compound of Formula RD (wherein RD is $R_4SO_2hal$) to give a compound of Formula XXIX (wherein RF is $R_4SO_2—$) can be carried out in the presence of a base, for example, triethylamine, N-ethyldiisopropylamine, N-methylmorpholine or pyridine, in an organic solvent, for example, dichloromethane, dichloroethane, carbon tetrachloride or chloroform.

The N-derivatization of a compound of Formula XXVIII with a compound of Formula RD (wherein RD is $(R_4)N═C(═Y)$) to give a compound of Formula XXIX (wherein RF is $(R_4)NH—C(═Y)—$) can be carried out optionally in the presence of a base, for example, triethylamine, N-ethyldiisopropylamine, N-methylmorpholine or pyridine, in an organic solvent for example, dichloromethane, dichloroethane, carbon tetrachloride or chloroform.

The deprotection of the secondary hydroxyl protecting group such as acyl group, of a compound of Formula XXIX to give a compound of Formula XXX can be carried out in presence of a base, for example, lithium hydroxide, sodium hydroxide, potassium hydroxide, in an organic solvent, for example, methanol, tetrahydrofuran, water or mixtures thereof.

The deprotection of a compound of Formula XXX to give a compound of Formula XXXI cab be carried out with acids, for example, trifluoroacetic acid or hydrochloric acid, in an organic solvent or a solvent system, for example, dichloromethane, chloroform, dichloroethane, THF or dioxane in water.

Scheme IV

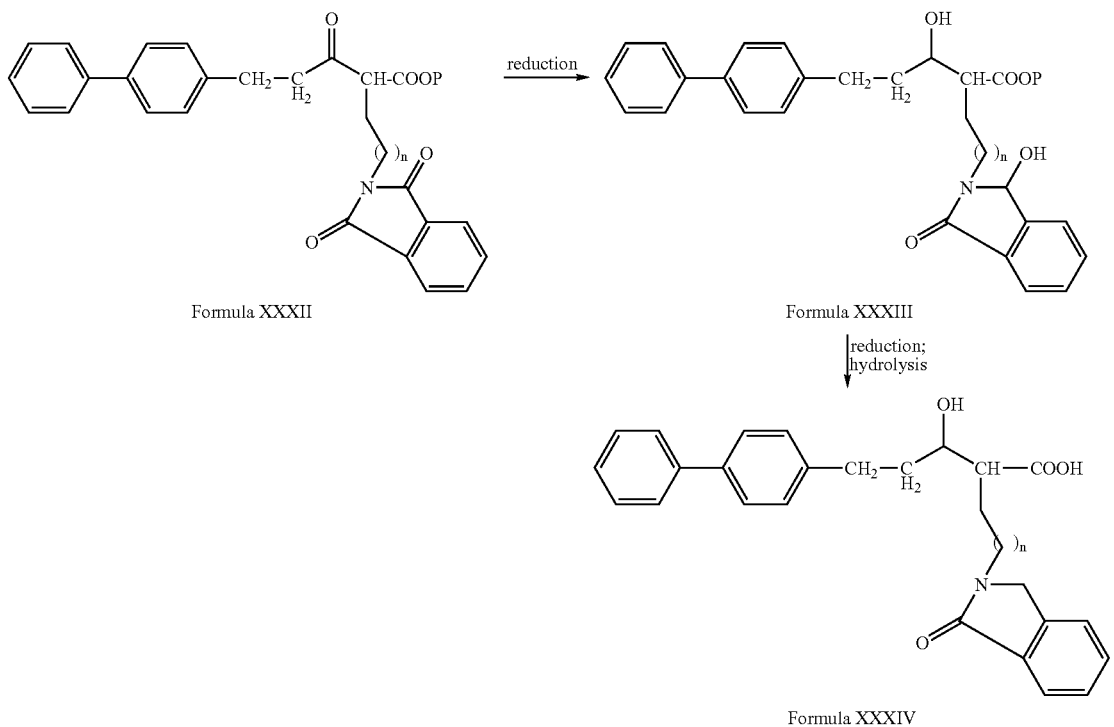

Formula XXXII

Formula XXXIII

Formula XXXIV

Compounds of Formula XXXIV can be prepared, for example, by following the synthetic route as depicted, for example, in Scheme IV. Thus a compound of Formula XXXII can undergo reduction to give a compound of Formula XXXIII, which can undergo ionic hydrogenation wherein C═O is reduced to $CH_2$ followed by hydrolysis to give a compound of Formula XXXIV.

The compound of Formula XXXII can undergo reduction to give a compound of Formula XXXIII in the presence of reducing agent, for example, sodium borohydride or lithium borohydride in organic solvent, for example, methanol, ethanol, propanol, isopropylalcohol and/or tetrahydrofuran.

The conversion of a compound of Formula XXXIII to a compound of Formula XXXIV can be carried out under ionic hydrogenation conditions wherein the C=O is reduced to CH$_2$ followed by in-situ hydrolysis of the ester (when P is t-butyl). Ionic hydrogenation conditions that may be carried out include reaction of a compound of Formula XXXIII with sodium borohydride or triethylsilane with acids, for example, trifluoroacetic acid in an organic solvent, for example, dichloromethane, dichloroethane or THF, and in-situ the acid-sensitive t-butyl group can be removed to provide a compound of Formula XXXIV.

The following illustrative compounds were prepared following Schemes I, II, III or IV described above:

5-Biphenyl-4-yl-3-hydroxy-2-[2-(4-oxo-1,2,3-benzotriazin-3(4H)-yl)ethyl]pentanoic acid (Compound No. 1),
5-(4'-tert-Butylbiphenyl-4-yl)-2-[2-(1,3-dioxo-1,3-dihydro-2H-isoindol-2-yl)ethyl]-3-hydroxypentanoic acid (Compound No. 2),
5-(4'-Butylbiphenyl-4-yl)-2-[2-(1,3-dioxo-1,3-dihydro-2H-isoindol-2-yl)ethyl]-3-hydroxypentanoic acid (Compound No. 3),
5-(4'-Chlorobiphenyl-4-yl)-2-[2-(1,3-dioxo-1,3-dihydro-2H-isoindol-2-yl)ethyl]-3-hydroxypentanoic acid (Compound No. 4),
2-[2-(1,3-Dioxo-1,3-dihydro-2H-isoindol-2-yl)ethyl]-3-hydroxy-5-(4'-trifluoromethoxybiphenyl-4-yl)pentanoic acid (Compound No. 5),
2-[2-(1,3-Dioxo-1,3-dihydro-2H-isoindol-2-yl)ethyl]-5-(4'-ethoxybiphenyl-4-yl)-3-hydroxypentanoic acid (Compound No. 6),
2-[2-(1,3-Dioxo-1,3-dihydro-2H-isoindol-2-yl)ethyl]-5-(4'-formylbiphenyl-4-yl)-3-hydroxypentanoic acid (Compound No. 7),
2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 8),
2-[2-(1,3-Dioxo-1,3-dihydro-2H-isoindol-2-yl)ethyl]-3-hydroxy-5-(4'-propoxybiphenyl-4-yl)pentanoic acid (Compound No. 9),
5-(3',4'-Difluorobiphenyl-4-yl)-2-[2-(1,3-dioxo-1,3-dihydro-2H-isoindol-2-yl)ethyl]-3-hydroxypentanoic acid (Compound No. 10),
2-(2-{[(Benzyloxy)carbonyl]amino}ethyl)-5-biphenyl-4-yl-3-hydroxypentanoicacid (Compound No. 11),
5-Biphenyl-4-yl-2-[2-(1,3-dioxo-1,3-dihydro-2H-isoindol-2-yl)ethyl]-3-hydroxypentanoic acid (Compound No. 12),
2-[2-(1,3-Dioxo-1,3-dihydro-2H-isoindol-2-yl)ethyl]-3-hydroxy-5-(4'-methoxybiphenyl-4-yl)pentanoic acid (Compound No. 23),
5-(2',3'-Dimethylbiphenyl-4-yl)-2-[2-(1,3-dioxo-1,3-dihydro-2H-isoindol-2-yl)ethyl]-3-hydroxypentanoic acid (Compound No. 24),
2-[2-(1,3-Dioxo-1,3-dihydro-2H-isoindol-2-yl)ethyl]-3-hydroxy-5-[3'-(trifluoromethyl)biphenyl-4-yl]pentanoic acid (Compound No. 25),
2-[2-(1,3-Dioxo-1,3-dihydro-2H-isoindol-2-yl)ethyl]-5-(4'-ethylbiphenyl-4-yl)-3-hydroxypentanoic acid (Compound No. 26),
5-(3',5'-Dichlorobiphenyl-4-yl)-2-[2-(1,3-dioxo-1,3-dihydro-2H-isoindol-2-yl)ethyl]-3-hydroxypentanoic acid (Compound No. 27),
5-[4'-Chloro-3'-(trifluoromethyl)biphenyl-4-yl]-2-[2-(1,3-dioxo-1,3-dihydro-2H-isoindol-2-yl)ethyl]-3-hydroxypentanoic acid (Compound No. 28),
5-(2',5'-Difluorobiphenyl-4-yl)-2-[2-(1,3-dioxo-1,3-dihydro-2H-isoindol-2-yl)ethyl]-3-hydroxypentanoic acid (Compound No. 29),
2-[2-(1,3-Dioxo-1,3-dihydro-2H-isoindol-2-yl)ethyl]-3-hydroxy-5-[2'-(trifluoromethoxy)biphenyl-4-yl]pentanoic acid (Compound No. 30),
2-[2-(1,3-Dioxo-1,3-dihydro-2H-isoindol-2-yl)ethyl]-3-hydroxy-5-[4'-(methylthio)biphenyl-4-yl]pentanoic acid (Compound No. 31),
2-[2-(1,3-Dioxo-1,3-dihydro-2H-isoindol-2-yl)ethyl]-5-(4'-fluoro-3'-methylbiphenyl-4-yl)-3-hydroxypentanoic acid (Compound No. 32),
2-[2-(1,3-Dioxo-1,3-dihydro-2H-isoindol-2-yl)ethyl]-3-hydroxy-5-(3'-isopropylbiphenyl-4-yl)pentanoic acid (Compound No. 33),
5-(3',4'-Dimethylbiphenyl-4-yl)-2-[2-(1,3-dioxo-1,3-dihydro-2H-isoindol-2-yl)ethyl]-3-hydroxypentanoic acid (Compound No. 34),
5-(2',6'-Difluorobiphenyl-4-yl)-2-[2-(1,3-dioxo-1,3-dihydro-2H-isoindol-2-yl)ethyl]-3-hydroxypentanoic acid (Compound No. 35),
2-[2-(1,3-Dioxo-1,3-dihydro-2H-isoindol-2-yl)ethyl]-5-(4'-fluorobiphenyl-4-yl)-3-hydroxypentanoic acid (Compound No. 36),
5-(3',5'-Difluorobiphenyl-4-yl)-2-[2-(1,3-dioxo-1,3-dihydro-2H-isoindol-2-yl)ethyl]-3-hydroxypentanoic acid (Compound No. 37),
5-(3'-Chloro-4'-fluorobiphenyl-4-yl)-2-[2-(1,3-dioxo-1,3-dihydro-2H-isoindol-2-yl)ethyl]-3-hydroxypentanoic acid (Compound No. 38),
5-(3',4'-Dimethoxybiphenyl-4-yl)-2-[2-(1,3-dioxo-1,3-dihydro-2H-isoindol-2-yl)ethyl]-3-hydroxypentanoic acid (Compound No. 39),
5-(3'-Chlorobiphenyl-4-yl)-2-[2-(1,3-dioxo-1,3-dihydro-2H-isoindol-2-yl)ethyl]-3-hydroxypentanoic acid (Compound No. 40),
2-[2-(1,3-Dioxo-1,3-dihydro-2H-isoindol-2-yl)ethyl]-3-hydroxy-5-(3'-methylbiphenyl-4-yl)pentanoic acid (Compound No. 41),
5-(2',3'-Difluorobiphenyl-4-yl)-2-[2-(1,3-dioxo-1,3-dihydro-2H-isoindol-2-yl)ethyl]-3-hydroxypentanoic acid (Compound No. 42),
2-[2-(1,3-Dioxo-1,3-dihydro-2H-isoindol-2-yl)ethyl]-5-(2'-fluoro-3'-methoxybiphenyl-4-yl)-3-hydroxypentanoic acid (Compound No. 43),
2-[2-(1,3-Dioxo-1,3-dihydro-2H-isoindol-2-yl)ethyl]-5-(3'-fluoro-4'-methylbiphenyl-4-yl)-3-hydroxypentanoic acid (Compound No. 44),
5-Biphenyl-4-yl-3-hydroxy-2-{2-[(phenylacetyl)amino]ethyl}pentanoic acid (Compound No. 45),
2-(3-Biphenyl-4-yl-1-hydroxypropyl)-6-(1,3-dioxo-1,3-dihydro-2H-isoindol-2-yl)hexanoic acid (Compound No. 46),
5-Biphenyl-4-yl-3-hydroxy-2-[2-(1-oxophthalazin-2(1H)-yl)ethyl]pentanoic acid (Compound No. 47),
5-Biphenyl-4-yl-2-[3-(1,3-dioxo-1,3-dihydro-2H-isoindol-2-yl)propyl]-3-hydroxypentanoic acid (Compound No. 48),
5-Biphenyl-4-yl-3-hydroxy-2-[2-(2'-oxospiro[cyclopropane-1,3'-indol]-1'(2'H)-yl)ethyl]pentanoic acid (Compound No. 49),
2-[2-(1,3-Dioxo-1,3-dihydro-2H-isoindol-2-yl)ethyl]-3-hydroxy-5-(4'-hydroxybiphenyl-4-yl)pentanoic acid (Compound No. 50), 3-Hydroxy-5-(4'-methoxybiphenyl-4-yl)-2-[2-(3-methyl-2, 6-dioxo-3,6-dihydropyrimidin-1(2H)-yl)ethyl]pentanoic acid (Compound No. 51), 5-(4'-Chlorobiphenyl-4-yl)-3-hydroxy-2-[2-(3-methyl-2,6-dioxo-3,6-dihydropyrimidin-1(2H)-yl)ethyl]pentanoic acid (Compound No. 52), 5-(4'-Fluorobiphenyl-4-yl)-3-hydroxy-2-[2-(3-methyl-2,6-dioxo-3,6-dihydropyrimidin-1(2H)-yl)ethyl]pentanoic acid (Compound No. 53), 5-[4-(5-Chloro-2-thienyl)phenyl]-2-[2-(1,3-dioxo-1,3-dihydro-2H-isoindol-2-yl)ethyl]-3-hydroxypentanoic acid (Compound No. 54), 4'-[4-Carboxy-6-(1,3-dioxo-1,3-dihydro-2H-isoindol-2-yl)-3-hydroxyhexyl]biphenyl-4-carboxylic acid (Compound No. 55), 2-[2-(1,3-Dioxo-1,3-dihydro-2H-isoindol-2-yl)ethyl]-3-hydroxy-5-[4'-(methoxycarbonyl)biphenyl-4-yl]pentanoic acid (Compound No. 56), 2-[2-(1,3-Dioxo-1,3-dihydro-2H-isoindol-2-yl)ethyl]-3-hydroxy-5-[4'-(trifluoromethyl)biphenyl-4-yl]pentanoic acid (Compound No. 57), 2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 58), 3-Hydroxy-2-[2-(4-oxo-1,2,3-benzotriazin-3(4H)-yl)ethyl]-5-[4'-(trifluoromethyl)biphenyl-4-yl]pentanoic acid (Compound No. 59), 5-(3',4'-Difluorobiphenyl-4-yl)-3-hydroxy-2-[2-(4-oxo-1,2,3-benzotriazin-3(4H)-yl)ethyl]pentanoic acid (Compound No. 60), 2-[2-(1,3-Dioxo-1,3-dihydro-2H-isoindol-2-yl)ethyl]-5-(3'-fluorobiphenyl-4-yl)-3-hydroxypentanoic acid (Compound No. 61), 5-[4'-(Benzyloxy)-3'-fluorobiphenyl-4-yl]-2-[2-(1,3-dioxo-1,3-dihydro-2H-isoindol-2-yl)ethyl]-3-hydroxypentanoic acid (Compound No. 62), 5-[4'-(Benzyloxy)biphenyl-4-yl]-2-[2-(1,3-dioxo-1,3-dihydro-2H-isoindol-2-yl)ethyl]-3-hydroxypentanoic acid (Compound No. 63), 3-Hydroxy-5-(4'-methoxybiphenyl-4-yl)-2-[2-(4-oxo-1,2,3-benzotriazin-3(4H)-yl)ethyl]pentanoic acid (Compound No. 64), 5-(4'-Chlorobiphenyl-4-yl)-3-hydroxy-2-[2-(4-oxo-1,2,3-benzotriazin-3(4H)-yl)ethyl]pentanoic acid (Compound No. 65), 2-[2-(1,3-Dioxo-1,3-dihydro-2H-isoindol-2-yl)ethyl]-3-hydroxy-5-(4'-methylbiphenyl-4-yl)pentanoic acid (Compound No. 66), 3-Hydroxy-5-[4-(6-methoxypyridin-3-yl)phenyl]-2-[2-(4-oxo-1,2,3-benzotriazin-3(4H)-yl)ethyl]pentanoic acid (Compound No. 67), 3-Hydroxy-5-(4'-methylbiphenyl-4-yl)-2-[2-(5-methyl-1,3-dioxo-1,3-dihydro-2H-isoindol-2-yl)ethyl]pentanoic acid (Compound No. 68), 5-(4'-Chlorobiphenyl-4-yl)-3-hydroxy-2-[2-(5-methyl-1,3-dioxo-1,3-dihydro-2H-isoindol-2-yl)ethyl]pentanoic acid (Compound No. 69), 3-Hydroxy-2-[2-(4-oxo-1,2,3-benzotriazin-3(4H)-yl)ethyl]-5-[4'-(trifluoromethoxy)biphenyl-4-yl]pentanoic acid (Compound No. 70), 5-(4'-Fluorobiphenyl-4-yl)-3-hydroxy-2-[2-(4-oxo-1,2,3-benzotriazin-3(4H)-yl)ethyl]pentanoic acid (Compound No. 71), 3-hydroxy-5-(4'-methylbiphenyl-4-yl)-2-[2-(4-oxo-1,2,3-benzotriazin-3(4H)-yl)ethyl]pentanoic acid (Compound No. 72), 5-(4'-Cyanobiphenyl-4-yl)-3-hydroxy-2-[2-(4-oxo-1,2,3-benzotriazin-3(4H)-yl)ethyl]pentanoic acid (Compound No. 73), 5-(4'-Fluorobiphenyl-4-yl)-3-hydroxy-2-[2-(5-methyl-1,3-dioxo-1,3-dihydro-2H-isoindol-2-yl)ethyl]pentanoic acid (Compound No. 74), 3-Hydroxy-5-[4-(6-methoxypyridin-3-yl)phenyl]-2-[2-(5-methyl-1,3-dioxo-1,3-dihydro-2H-isoindol-2-yl)ethyl]pentanoic acid (Compound No. 75), 5-(4'-Ethylbiphenyl-4-yl)-3-hydroxy-2-[2-(4-oxo-1,2,3-benzotriazin-3(4H)-yl)ethyl]pentanoic acid (Compound No. 76), 3-Hydroxy-2-[2-(5-methyl-1,3-dioxo-1,3-dihydro-2H-isoindol-2-yl)ethyl]-5-[4'-(trifluoromethyl)biphenyl-4-yl]pentanoic acid (Compound No. 77), 5-Biphenyl-4-yl-3-hydroxy-2-[2-(1-oxo-4-phenyl-4a,8a-dihydrophthalazin-2(1H)-yl)ethyl]pentanoic acid (Compound No. 84).

5-Biphenyl-4-yl-3-hydroxy-2-[2-(3-oxo-2,3-dihydro-4H-1,4-benzoxazin-4-yl)ethyl]pentanoic acid (Compound No. 85), 5-Biphenyl-4-yl-2-{2-[(3aR,7aS)-1,3-dioxo-1,3,3a,4,7,7a-hexahydro-2H-isoindol-2-yl]ethyl}-3-hydroxypentanoic acid (Compound No. 86), 5-Biphenyl-4-yl-2-(2-{[(4-fluorophenyl)sulfonyl]amino}ethyl)-3-hydroxypentanoic acid (Compound No. 87), 5-Biphenyl-4-yl-2-(2-{[(3-fluorophenyl)acetyl]amino}ethyl)-3-hydroxypentanoic acid (Compound No. 88), 5-Biphenyl-4-yl-2-{2-[(4-fluorobenzoyl)amino]ethyl}-3-hydroxypentanoic acid (Compound No. 89), 5-Biphenyl-4-yl-3-hydroxy-2-[2-(5-methyl-1,3-dioxo-1,3-dihydro-2H-isoindol-2-yl)ethyl]pentanoic acid (Compound No. 90), 5-Biphenyl-4-yl-3-hydroxy-2-[2-(1-oxo-1,3-dihydro-2H-isoindol-2-yl)ethyl]pentanoic acid (Compound No. 91).

5-Biphenyl-4-yl-2-[2-({[(4-fluorophenyl)amino]carbonyl}amino)ethyl]-3-hydroxypentanoic acid (Compound No. 92), 5-Biphenyl-4-yl-2-[2-(4,4-dimethyl-2,6-dioxopiperidin-1-yl)ethyl]-3-hydroxypentanoic acid (Compound No. 93), 5-Biphenyl-4-yl-2-[2-(7,9-dioxo-8-azaspiro[4.5]dec-8-yl)ethyl]-3-hydroxypentanoic acid (Compound No. 94), 2-(3-Biphenyl-4-yl-1-hydroxypropyl)pent-4-ynoic acid (Compound No. 95);

5-Biphenyl-4-yl-3-hydroxy-2-[2-(2-oxo-1,3-benzoxazol-3(2H)-yl)ethyl]pentanoic acid (Compound No. 96), 2-[2-(5-tert-Butyl-1,3-dioxo-1,3-dihydro-2H-isoindol-2-yl)ethyl]-3-hydroxy-5-[4-(6-methoxypyridin-3-yl)phenyl]pentanoic acid (Compound No. 97), 5-{4-[6-(Dimethylamino)pyridin-3-yl]phenyl}-2-[2-(1,3-dioxo-1,3-dihydro-2H-isoindol-2-yl)ethyl]-3-hydroxypentanoic acid (Compound No. 98), 2-[2-(1,3-Dioxo-1,3-dihydro-2H-isoindol-2-yl)ethyl]-3-hydroxy-5-[4'-(methylsulfonyl)biphenyl-4-yl]pentanoic acid (Compound No. 99), 5-[4'-(Aminocarbonyl)biphenyl-4-yl]-2-[2-(1,3-dioxo-1,3-dihydro-2H-isoindol-2-yl)ethyl]-3-hydroxypentanoic acid (Compound No. 100), 5-[4-(1-Benzyl-1H-pyrazol-4-yl)phenyl]-2-[2-(1,3-dioxo-1,3-dihydro-2H-isoindol-2-yl)ethyl]-3-hydroxypentanoic acid (Compound No. 101), 5-Biphenyl-4-yl-2-[2-(5,6-dichloro-1,3-dioxo-1,3-dihydro-2H-isoindol-2-yl)ethyl]-3-hydroxypentanoic acid (Compound No. 102), 5-Biphenyl-4-yl-2-[2-(2,4-dioxo-1,4-dihydroquinazolin-3 (2H)-yl)ethyl]-3-hydroxypentanoic acid (Compound No. 103), 5-Biphenyl-4-yl-2-[2-(1,3-dioxo-1,3-dihydro-2H-pyrrolo[3,4-c]pyridin-2-yl)ethyl]-3-hydroxypentanoic acid (Compound No. 104), 2-[2-(5-tert-Butyl-1,3-dioxo-1,3-dihydro-2H-isoindol-2-yl) ethyl]-5-(3',4'-difluorobiphenyl-4-yl)-3-hydroxypentanoic acid (Compound No. 105), 2-[2-(1,3-Dioxo-1,3-dihydro-2H-isoindol-2-yl)ethyl]-3-hydroxy-5-(4-pyrimidin-5-ylphenyl)pentanoic acid (Compound No. 119), 5-Biphenyl-4-yl-3-hydroxy-2-[2-(7-methyl-4-oxo-1,2,3-benzotriazin-3(4H)-yl)ethyl]pentanoic acid (Compound No. 120), 5-Biphenyl-4-yl-2-[2-(5-tert-butyl-1,3-dioxo-1,3-dihydro-2H-isoindol-2-yl)ethyl]-3-hydroxypentanoic acid (Compound No. 121), and 5-Biphenyl-4-yl-3-hydroxy-2-[2-(1-oxo-1,3-dihydro-2H-isoindol-2-yl)butyl]pentanoic acid (Compound No. 124).

In the above schemes, where specific bases, acids, solvents, condensing agents, reducing agent, deprotecting agent, hydrolyzing agents, metal catalysts etc., are mentioned, it is to be understood that other acids, bases, solvents, condensing agents, reducing agent, deprotecting agent, hydrolyzing agents, metal catalysts etc., known to those skilled in the art may also be used. Similarly, the reaction temperature and duration of the reactions may be adjusted according to the requirements that arise during the process.

The compounds prepared by above Schemes I to IV may contain one or more asymmetric carbon atoms and were separated into diastereomer pairs or single diastereomers by preparative thin layer chromatography and/or by HPLC, using an achiral or chiral column as required.

The following illustrative compounds were separated into diastereomer pairs or single diastereomers:

(2R,3S+2S,3R)-2-[2-(1,3-Dioxo-1,3-dihydro-2H-isoindol-2-yl)ethyl]-5-(4'-formylbiphenyl-4-yl)-3-hydroxypentanoic acid (Compound No. 13), (2R,3R+2S,3S)-2-[2-(1,3-Dioxo-1,3-dihydro-2H-isoindol-2-yl)ethyl]-5-(4'-formylbiphenyl-4-yl)-3-hydroxypentanoic acid (Compound No. 14), (2R,3R+2S,3S)-2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 15), (2R,3S+2S,3R)-2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 16), (2R,3S+2S,3R)-5-(4'-Acetylbiphenyl-4-yl)-2-[2-(1,3-dioxo-1,3-dihydro-2H-isoindol-2-yl)ethyl]-3-hydroxypentanoic acid (Compound No. 17), (2R,3R+2S,3S)-5-(4'-Acetylbiphenyl-4-yl)-2-[2-(1,3-dioxo-1,3-dihydro-2H-isoindol-2-yl)ethyl]-3-hydroxypentanoic acid (Compound No. 18), (2R,3S+2S,3R)-2-[2-(1,3-Dioxo-1,3-dihydro-2H-isoindol-2-yl)ethyl]-3-hydroxy-5-(4'-propoxybiphenyl-4-yl)pentanoic acid (Compound No. 19), (2R,3R+2S,3S)-2-[2-(1,3-Dioxo-1,3-dihydro-2H-isoindol-2-yl)ethyl]-3-hydroxy-5-(4'-propoxybiphenyl-4-yl)pentanoic acid (Compound No. 20), (2R,3S+2S,3R)-5-(3',4'-Difluorobiphenyl-4-yl)-2-[2-(1,3-dioxo-1,3-dihydro-2H-isoindol-2-yl)ethyl]-3-hydroxypentanoic acid (Compound No. 21), (2R,3R+2S,3S)-5-(3',4'-Difluorobiphenyl-4-yl)-2-[2-(1,3-dioxo-1,3-dihydro-2H-isoindol-2-yl)ethyl]-3-hydroxypentanoic acid (Compound No. 22), (2R,3S+2S,3R)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 78), (2R,3R+2S,3S)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 79), (2R,3R+2S,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 80), (2R,3S+2S,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 81), (2R,3S+2S,3R)-2-[2-(1,3-Dioxo-1,3-dihydro-2H-isoindol-2-yl)ethyl]-5-(4'-fluorobiphenyl-4-yl)-3-hydroxypentanoic acid (Compound No. 82), (2R,3R+2S,3S)-2-[2-(1,3-Dioxo-1,3-dihydro-2H-isoindol-2-yl)ethyl]-5-(4'-fluorobiphenyl-4-yl)-3-hydroxypentanoic acid (Compound No. 83), (2R,3S+2S,3R)-2-[2-(5-tert-Butyl-1,3-dioxo-1,3-dihydro-2H-isoindol-2-yl)ethyl]-5-(4'-fluorobiphenyl-4-yl)-3-hydroxypentanoic acid (Compound No. 106), (2R,3S+2S,3R)-2-[2-(5-tert-Butyl-1,3-dioxo-1,3-dihydro-2H-isoindol-2-yl)ethyl]-3-hydroxy-5-[4'-(trifluoromethyl)biphenyl-4-yl]pentanoic acid (Compound No. 107), (2R,3R+2S,3S)-2-[2-(5-tert-Butyl-1,3-dioxo-1,3-dihydro-2H-isoindol-2-yl)ethyl]-5-(4'-fluorobiphenyl-4-yl)-3-hydroxypentanoic acid (Compound No. 108), (2R,3R+2S,3S)-2-[2-(5-tert-Butyl-1,3-dioxo-1,3-dihydro-2H-isoindol-2-yl)ethyl]-3-hydroxy-5-[4'-(trifluoromethyl)biphenyl-4-yl]pentanoic acid (Compound No. 109), 2-[2-(1,3-Dioxo-1,3-dihydro-2H-isoindol-2-yl)ethyl]-5-(3'-fluoro-4'-methoxybiphenyl-4-yl)-3-hydroxypentanoic acid (Compound No. 110), (2R,3S+2S,3R)-2-[2-(1,3-Dioxo-1,3-dihydro-2H-isoindol-2-yl)ethyl]-3-hydroxy-5-[4-(6-methylpyridin-3-yl)phenyl]pentanoic acid (Compound No. 111), (2R,3R+2S,3S)-2-[2-(1,3-Dioxo-1,3-dihydro-2H-isoindol-2-yl)ethyl]-3-hydroxy-5-[4-(6-methylpyridin-3-yl)phenyl]pentanoic acid (Compound No. 112), (2R,3R+2S,3S)-2-[2-(5-tert-Butyl-1,3-dioxo-1,3-dihydro-2H-isoindol-2-yl)ethyl]-3-hydroxy-5-(4'-methylbiphenyl-4-yl)pentanoic acid (Compound No. 113), (2R,3S+2S,3R)-2-[2-(5-tert-Butyl-1,3-dioxo-1,3-dihydro-2H-isoindol-2-yl)ethyl]-3-hydroxy-5-(4'-methylbiphenyl-4-yl)pentanoic acid (Compound No. 114), (2R,3S+2S,3S)-2-[2-(5-tert-Butyl-1,3-dioxo-1,3-dihydro-2H-isoindol-2-yl)ethyl]-3-hydroxy-5-(4'-methoxybiphenyl-4-yl)pentanoic acid (Compound No. 115), (2R,3R+2S,3S)-2-[2-(5-tert-Butyl-1,3-dioxo-1,3-dihydro-2H-isoindol-2-yl)ethyl]-5-(4'-chlorobiphenyl-4-yl)-3-hydroxypentanoic acid (Compound No. 116), (2R,3S+2S,3R)-2-[2-(5-tert-Butyl-1,3-dioxo-1,3-dihydro-2H-isoindol-2-yl)ethyl]-5-(4'-chlorobiphenyl-4-yl)-3-hydroxypentanoic acid (Compound No. 117), (2R,3S+2S,3R)-2-[2-(5-tert-Butyl-1,3-dioxo-1,3-dihydro-2H-isoindol-2-yl)ethyl]-3-hydroxy-5-(4'-methoxybiphenyl-4-yl)pentanoic acid (Compound No. 118), (2R,3S+2S,3R)-5-biphenyl-4-yl-3-hydroxy-2-[2-(1H-indol-3-yl)ethyl]pentanoic acid (Compound No. 122), (2R,3R+2S,3S)-5-biphenyl-4-yl-3-hydroxy-2-[2-(1H-indol-3-yl)ethyl]pentanoic acid (Compound No. 123), (2R,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 125), (2S,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 126),
(2R,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 127),
(2S,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 128),
(2R,3S)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 129),
(2S,3R)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 130),
(2R,3R)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 131),
(2S,3S)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 132),
(2R,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 133),
(2S,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 134),
(2R,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 135), and
(2S,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 136).

Examples set forth demonstrates the general synthetic procedure for the preparation of representative compounds. The examples are provided to illustrate particular aspect of the disclosure and do not limit the scope of the present invention

EXPERIMENTAL

General Procedure

Synthesis of 3-(2-bromoethyl)-1,2,3-benzotriazin-4(3H)-one

To a solution of the compound 1,2,3-benzotriazin-4(3H)-one (500 mg) (commercially available) in dimethylformamide (13 ml) was added anhydrous potassium carbonate (2.8 g) and stirred for 20 minutes. To it was added dibromoethane (2 g) and stirred the reaction mixture first at room temperature for few minutes and then at 60° C. for 2 hours. The solid thus obtained was filtered and the filtrate was concentrated under reduced pressure. The residue thus obtained was diluted with water and extracted with ethylacetate. The organic layer was separated, washed with water and brine and dried over anhydrous sodium sulphate. The solvent was evaporated under reduced pressure and the residue thus obtained was purified by column chromatography using 20% ethyl acetate in hexane as eluant to furnish the title compound (590 mg).

Synthesis of 4-(bromomethyl)biphenyl

Carbon tetrabromide (8.99 g) and triphenylphosphine (7.11 g) were added to a stirred solution of biphenyl-4-yl-methanol (5.00 g) in dichloromethane (100 ml) at room temperature and stirred the reaction mixture for approximately 2 hours at the same temperature. The solvent was evaporated under reduced pressure and the residue thus obtained was purified by column chromatography using 5% diethylether in hexane as eluant to furnish the title compound (6.37 g).

Scheme I, Procedure:

Example 1

Synthesis of 5-biphenyl-4-yl-3-hydroxy-2-[2-(4-oxo-1,2,3-benzotriazin-3(4H)-yl)ethyl]-pentanoic acid (Compound No. 1)

Step 1: Synthesis of tert-butyl 5-biphenyl-4-yl-3-oxopentanoate

A solution of tert-butyl acetoacetate (7.2 g) in tetrahydrofuran (80 ml) was added to a stirred solution of sodium hydride (1.33 g) in tetrahydrofuran (60 ml) at 0° C. under nitrogen atmosphere. The reaction mixture was stirred for 10 minutes followed by the addition of n-butyl lithium (23 ml, 2.5 M solution in hexane) dropwise over 10 minutes. The resulting reaction mixture was stirred for 10 minutes. A solution of 4-(bromomethyl) biphenyl (12.5 g) in tetrahydrofuran (60 ml) was added over 10 minutes and the resulting solution was stirred at 0° C. for approximately 2 hours. To resulting mixture was added hydrochloric acid (6 M, 15 ml) followed by extracting the mixture with diethyl ether. The organic layers were combined, washed with water and brine and dried over anhydrous sodium sulphate. The solvent was evaporated under reduced pressure and the residue thus obtained was purified by silica gel column chromatography using 8% ethyl acetate-hexane as eluant to furnish the title compound (7.5 g).

Step 2: Synthesis of tert-butyl 5-biphenyl-4-yl-3-oxo-2-[2-(4-oxo-1,2,3-benzotriazin-3(4H)-yl)ethyl]pentanoate To a solution of the compound (300 mg) obtained from step 1 above in dry tetrahydrofuran (4 ml) and tert-butanol (4 ml) at 0° C. was added potassium tert-butoxide (104 mg) and stirred for 20 minutes. To the resulting reaction mixture was added 3-(2-bromoethyl)-1,2,3-benzotriazin-4(3H)-one (235 mg) and tetrabutylammonium iodide (349 mg) and the mixture was further stirred for 30 minutes at 0° C., followed by stirring at room temperature for 30 minutes and finally at 80° C. for about 5-6 hours. The solvent was evaporated under reduced pressure and the residue thus obtained was diluted with water and extracted with ethyl acetate. The organic layer was washed with water and brine, dried over anhydrous sodium sulphate and filtered. The solvent was evaporated under reduced pressure and the residue thus obtained was purified by column chromatography using 20% ethyl acetate in hexane as eluant to furnish the title compound (240 mg).

Step 3: Synthesis of tert-butyl 5-biphenyl-4-yl-3-hydroxy-2-[2-(4-oxo-1,2,3-benzotriazin-3(4H)-yl)ethyl]pentanoate To a solution of the compound (240 mg) obtained form step 2 above in methanol (4-5 ml) at −10° C. was added sodium borohydride (44 mg). The reaction mixture was stirred for 2 hours at −10° C. to −2° C. The solvent was evaporated under reduced pressure and the residue thus obtained was taken in saturated ammonium chloride and extracted with ethyl acetate. The organic layer was washed with water and brine and dried over anhydrous sodium sulphate and concentrated under reduced pressure. The residue thus obtained was purified by column chromatography using 30% ethyl acetate in hexane as eluant to furnish the title compound (100 mg).

Step 4: Synthesis of 5-biphenyl-4-yl-3-hydroxy-2-[2-(4-oxo-1,2,3-benzotriazin-3(4H)-yl)ethyl]pentanoic acid To a solution of the compound (100 mg) obtained from step 3 above in dichloromethane (2 ml) at 0° C. was added trifluoroacetic acid (8 ml) and stirred the reaction mixture for about 2-3 hours and then at room temperature for 3 hours. The solvent and excess reagents were evaporated under reduced pressure and the residue thus obtained was purified by preparative thin layer chromatography (eluant-ethyl acetate) to furnish the title compound (40 mg).

Mass (m/z): 444.1 ($M^+$+1).

The following illustrative analogues were prepared analogously:

5-Biphenyl-4-yl-2-[2-(1,3-dioxo-1,3-dihydro-2H-isoindol-2-yl)ethyl]-3-hydroxypentanoic acid (Compound No. 12),
2-(3-Biphenyl-4-yl-1-hydroxypropyl)-6-(1,3-dioxo-1,3-dihydro-2H-isoindol-2-yl)hexanoic acid (Compound No. 46),
5-Biphenyl-4-yl-3-hydroxy-2-[2-(1-oxophthalazin-2(1H)-yl)ethyl]pentanoic acid (Compound No. 47),
5-Biphenyl-4-yl-2-[3-(1,3-dioxo-1,3-dihydro-2H-isoindol-2-yl)propyl]-3-hydroxypentanoic acid (Compound No. 48),
5-Biphenyl-4-yl-3-hydroxy-2-[2-(2'-oxospiro[cyclopropane-1,3'-indol]-1'(2'H)-yl)ethyl]pentanoic acid (Compound No. 49),
5-Biphenyl-4-yl-3-hydroxy-2-[2-(1-oxo-4-phenyl-4a,8a-dihydrophthalazin-2(1H)-yl)ethyl]pentanoic acid (Compound No. 84).
5-Biphenyl-4-yl-3-hydroxy-2-[2-(3-oxo-2,3-dihydro-4H-1,4-benzoxazin-4-yl)ethyl]pentanoic acid (Compound No. 85),
5-Biphenyl-4-yl-2-{2-[(3aR,7aS)-1,3-dioxo-1,3,3a,4,7,7a-hexahydro-2H-isoindol-2-yl]ethyl}-3-hydroxypentanoic acid (Compound No. 86),
5-Biphenyl-4-yl-3-hydroxy-2-[2-(5-methyl-1,3-dioxo-1,3-dihydro-2H-isoindol-2-yl)ethyl]pentanoic acid (Compound No. 90),
5-Biphenyl-4-yl-2-[2-(4,4-dimethyl-2,6-dioxopiperidin-1-yl)ethyl]-3-hydroxypentanoic acid (Compound No. 93),
5-Biphenyl-4-yl-2-[2-(7,9-dioxo-8-azaspiro[4.5]dec-8-yl)ethyl]-3-hydroxypentanoic acid (Compound No. 94),
2-(3-Biphenyl-4-yl-1-hydroxypropyl)pent-4-ynoic acid (Compound No. 95);
5-Biphenyl-4-yl-3-hydroxy-2-[2-(2-oxo-1,3-benzoxazol-3(2H)-yl)ethyl]pentanoic acid (Compound No. 96)
5-Biphenyl-4-yl-2-[2-(5,6-dichloro-1,3-dioxo-1,3-dihydro-2H-isoindol-2-yl)ethyl]-3-hydroxypentanoic acid (Compound No. 102),
5-Biphenyl-4-yl-2-[2-(2,4-dioxo-1,4-dihydroquinazolin-3(2H)-yl)ethyl]-3-hydroxypentanoic acid (Compound No. 103),
5-Biphenyl-4-yl-2-[2-(1,3-dioxo-1,3-dihydro-2H-pyrrolo[3,4-c]pyridin-2-yl)ethyl]-3-hydroxypentanoic acid (Compound No. 104),
5-Biphenyl-4-yl-3-hydroxy-2-[2-(7-methyl-4-oxo-1,2,3-benzotriazin-3(4H)-yl)ethyl]pentanoic acid (Compound No. 120), and
5-Biphenyl-4-yl-2-[2-(5-tert-butyl-1,3-dioxo-1,3-dihydro-2H-isoindol-2-yl)ethyl]-3-hydroxypentanoic acid (Compound No. 121).

Scheme II, Procedure:

Example 2

Synthesis of 5-(4'-chlorobiphenyl-4-yl)-2-[2-(1,3-dioxo-1,3-dihydro-2H-isoindol-2-yl)ethyl]-3-hydroxypentanoic acid (Compound No. 4)

Step 1: Synthesis of 5-(4-bromo-phenyl)-3-oxo-pentanoic acid tert-butyl ester tert-Butyl acetoacetate (23.8 ml) was added dropwise over 15 minutes to a stirred suspension of sodium hydride (8.9 mg) in tetrahydrofuran at 0° C. under nitrogen atmosphere. After stirring for 20 minutes n-butyl lithium in hexane (111 ml) was added then stirring continued for a further ten minutes. The resulting solution was treated dropwise with a solution of 4-bromobenzyl bromide (14.19 g) in tetrahydrofuran (100 ml) and then warmed to room temperature. The reaction was stirred for 40 minutes at room temperature and then quenched with HCl (6M, 5 ml). The resulting mixture was extracted with diethyl ether. The organic phases were combined, washed with brine and dried over anhydrous sodium sulphate. The solvent was evaporated under reduced pressure. The residue was thus obtained was purified via flash chromatography using 5% ethyl acetate in hexane as eluant to furnish the title compound (37 g).

Step 2: Synthesis of 1,1-dimethylethyl 2-(2-{[(1,1-dimethylethyl)(dimethyl)silyl]oxy}ethyl)-5-(4-bromophenyl)-3-oxopentanoate A solution of the compound (9.7 g) obtained from step 1 above in dimethylformamide (25 ml) was added dropwise over 20 minutes to a stirred suspension of sodium hydride (1.42 g) in dimethylformamide (25 ml) at 0° C. under nitrogen atmosphere and stirred the reaction mixture for 20 minutes. To it was added (2-bromoethoxy)-t-butyldimethylsilane (8.50 g) dropwise over 20 minutes at 0° C. then the reaction mixture was heated to 70° C. for about 3-4 hour. On cooling to room temperature the reaction was quenched with water. The residue was partitioned between saturated aqueous ammonium chloride solution and dichloromethane. The organic phases were combined, washed with water and brine, dried over anhydrous sodium sulphate and concentrated under reduced pressure. The residue thus obtained was purified by column chromatography using 8% ethyl acetate in hexane as eluant to furnish the title compound (9.5 g).

Step 3: Synthesis of 1,1-dimethylethyl 2-(2-{[(1,1-dimethylethyl)(dimethyl)silyl]oxy}ethyl)-3-hydroxy-5-(bromophenyl)pentanoate Sodium borohydride (0.46 g) was added portion wise to a stirred solution of the compound (4.2 g) obtained from step 2 above in methanol (50 ml) at 0° C. under nitrogen atmosphere and stirred the reaction mixture for approximately 2 hours. The mixture was quenched with saturated aqueous ammonium chloride solution (100 ml) and extracted with diethyl ether. The organic layers were combined, washed with water and brine, dried over anhydrous sodium sulphate and concentrated under reduced pressure. The residue thus obtained was purified by column chromatography using 25% ethyl acetate in hexane as eluant to furnish the title compound (3.7 g).

Step 4: Synthesis of 1,1-dimethylethyl 2-(2-{[(1,1-dimethylethyl)(dimethyl)silyl]oxy}ethyl)-5-(4-bromophenyl)-3-({[4-(methyloxy)phenyl]methyl}oxy) pentanoate Boron trifluoride etherate (5.0 ml) was added to a stirred solution of the compound (4.0 g) obtained from step 3 above and 4-methoxybenzyl 2,2,2-trichloroethanimidoate (3.26 g) in tetrahydrofuran (40 ml) at 0° C. under nitrogen atmosphere. The reaction was allowed to warm to room temperature at which stirring was continued for 2 hour. The solvent was evaporated under reduced pressure and the residue thus obtained was purified by column chromatography using 20% ethyl acetate in hexane as eluant to furnish the title compound (3.8 g).

Step 5: Synthesis of 1,1-dimethylethyl 2-(2-hydroxyethyl)-5-(4-bromophenyl)-3-({[4-(methyloxy)phenyl]methyl}oxy)pentanoate A solution of tetra-n-butylammonium fluoride (0.45 ml) was added dropwise over 15 minutes to a stirred solution of the compound (200 mg) obtained from step 4 above in tetrahydrofuran (5 ml) at 0° C. under nitrogen atmosphere. The reaction mixture was allowed to warm to room temperature at which stirring was continued for 2 hour. The volatiles were evaporated under reduced pressure and the residue thus obtained was partitioned between ethyl acetate and water. The phases were separated and the aqueous layer was washed with ethyl acetate. The organic layers were combined, washed with water and brine, dried over anhydrous sodium sulphate and concentrated under reduced pressure to furnish the title compound (120 mg).

Step 6: Synthesis of 1,1-Dimethylethyl)5-(4-bromophenyl)-3-({[4-(methyloxy)phenyl]methyl}oxy)-2-{2-[(methylsulfonyl)oxy]ethyl}pentanoate Methanesulfonyl chloride (0.63 ml) was added in one portion to a stirred solution of the compound (2.99 g) obtained from step 5 above and triethylamine (2.6 ml) in dichloromethane (50 ml) at room temperature under nitrogen atmosphere and stirred at room temperature for 1 hour. The crude mixture was partitioned between saturated aqueous citric acid solution and dichloromethane. The phases were separated and the organic layer was concentrated under reduced pressure to furnish the title compound (3.2 g).

Step 7: Synthesis of 1,1-Dimethylethyl 2-[2-(1,3-dioxo-1,3-dihydro-2H-isoindol-2-yl)ethyl]-5-(4-bromophenyl)-3-({[4-(methyloxy)phenyl]methyl}oxy)pentanoate Potassium phthalimide (1.25 g) was added in one portion to a stirred solution of the compound (3.5 g) obtained from step 6 above in dimethylformamide (25 ml) at room temperature under nitrogen atmosphere. The resulting solution was heated at 80° C. for about 2 hours and then cooled to room temperature. The volatiles were evaporated under reduced pressure and the residue thus obtained was partitioned between dichloromethane and water. The layers were separated and the organic phase evaporated to dryness under reduced pressure.

The residue thus obtained was purified by column chromatography using 20% ethyl acetate in hexane as eluant to furnish the title compound (2.45 g).

Step 8: Synthesis of tert-butyl 5-(4'-chlorobiphenyl-4-yl)-2-[2-(1,3-dioxo-1,3-dihydro-2H-isoindol-2-yl) ethyl]-3-[(4-methoxybenzyl)oxy]pentanoate To a solution of the compound (200 mg) obtained from step 7 above, (4-chlorophenyl)boronic acid (90 mg) and potassium carbonate (133 mg) in dimethylformamide (3 ml) was added tetrakis(triphenylphosphine)palladium (0) (18.5 mg) and stirred the reaction mixture for 6 hours at about 100° C. The resulting reaction mixture was diluted with water and extracted with ethyl acetate. The organic layer was separated, washed with water and brine, dried over anhydrous sodium sulphate and concentrated under reduced pressure. The residue thus obtained was purified by column chromatography using 20% ethyl acetate in hexane as eluant to furnish the title compound (116 mg).

Step 9: Synthesis of 5-(4'-chlorobiphenyl-4-yl)-2-[2-(1,3-dioxo-1,3-dihydro-2H-isoindol-2-yl)ethyl]-3-hydroxypentanoic acid To a solution of the compound (120 mg) obtained from step 8 above in dichloromethane (5 ml) was added trifluoroacetic acid (2 ml) and stirred the reaction mixture for 2 hours at room temperature. The solvent was evaporated under reduced pressure and the residue thus obtained was purified by preparative thin layer chromatography (eluant: 60% ethyl acetate in hexane) to furnish the title compound (68 mg).

Mass (m/z): 478.0 (M$^+$+1).

The following illustrative compounds were prepared analogously:

5-(4'-tert-Butylbiphenyl-4-yl)-2-[2-(1,3-dioxo-1,3-dihydro-2H-isoindol-2-yl)ethyl]-3-hydroxypentanoic acid (Compound No. 2), 5-(4'-Butylbiphenyl-4-yl)-2-[2-(1,3-dioxo-1,3-dihydro-2H-isoindol-2-yl)ethyl]-3-hydroxypentanoic acid (Compound No. 3), 2-[2-(1,3-Dioxo-1,3-dihydro-2H-isoindol-2-yl)ethyl]-3-hydroxy-5-(4'-methoxybiphenyl-4-yl)pentanoic acid (Compound No. 5), 2-[2-(1,3-Dioxo-1,3-dihydro-2H-isoindol-2-yl)ethyl]-5-(4'-ethoxybiphenyl-4-yl)-3-hydroxypentanoic acid (Compound No. 6), 2-[2-(1,3-Dioxo-1,3-dihydro-2H-isoindol-2-yl)ethyl]-5-(4'-formylbiphenyl-4-yl)-3-hydroxypentanoic acid (Compound No. 7), 2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 8), 2-[2-(1,3-Dioxo-1,3-dihydro-2H-isoindol-2-yl)ethyl]-3-hydroxy-5-(4'-propoxybiphenyl-4-yl)pentanoic acid (Compound No. 9), 5-(3',4'-Difluorobiphenyl-4-yl)-2-[2-(1,3-dioxo-1,3-dihydro-2H-isoindol-2-yl)ethyl]-3-hydroxypentanoic acid (Compound No. 10), 2-[2-(1,3-Dioxo-1,3-dihydro-2H-isoindol-2-yl)ethyl]-3-hydroxy-5-(4'-methoxybiphenyl-4-yl)pentanoic acid (Compound No. 23), 5-(2',3'-Dimethylbiphenyl-4-yl)-2-[2-(1,3-dioxo-1,3-dihydro-2H-isoindol-2-yl)ethyl]-3-hydroxypentanoic acid (Compound No. 24), 2-[2-(1,3-Dioxo-1,3-dihydro-2H-isoindol-2-yl)ethyl]-3-hydroxy-5-[3'-(trifluoromethyl)biphenyl-4-yl]pentanoic acid (Compound No. 25), 2-[2-(1,3-Dioxo-1,3-dihydro-2H-isoindol-2-yl)ethyl]-5-(4'-ethylbiphenyl-4-yl)-3-hydroxypentanoic acid (Compound No. 26), 5-(3',5'-Dichlorobiphenyl-4-yl)-2-[2-(1,3-dioxo-1,3-dihydro-2H-isoindol-2-yl)ethyl]-3-hydroxypentanoic acid (Compound No. 27), 5-[4'-Chloro-3'-(trifluoromethyl)biphenyl-4-yl]-2-[2-(1,3-dioxo-1,3-dihydro-2H-isoindol-2-yl)ethyl]-3-hydroxypentanoic acid (Compound No. 28), 5-(2',5'-Difluorobiphenyl-4-yl)-2-[2-(1,3-dioxo-1,3-dihydro-2H-isoindol-2-yl)ethyl]-3-hydroxypentanoic acid (Compound No. 29), 2-[2-(1,3-Dioxo-1,3-dihydro-2H-isoindol-2-yl)ethyl]-3-hydroxy-5-[2'-(trifluoromethoxy)biphenyl-4-yl]pentanoic acid (Compound No. 30), 2-[2-(1,3-Dioxo-1,3-dihydro-2H-isoindol-2-yl)ethyl]-3-hydroxy-5-[4'-(methylthio)biphenyl-4-yl]pentanoic acid (Compound No. 31), 2-[2-(1,3-Dioxo-1,3-dihydro-2H-isoindol-2-yl)ethyl]-5-(4'-fluoro-3'-methylbiphenyl-4-yl)-3-hydroxypentanoic acid (Compound No. 32), 2-[2-(1,3-Dioxo-1,3-dihydro-2H-isoindol-2-yl)ethyl]-3-hydroxy-5-(3'-isopropylbiphenyl-4-yl)pentanoic acid (Compound No. 33), 5-(3',4'-Dimethylbiphenyl-4-yl)-2-[2-(1,3-dioxo-1,3-dihydro-2H-isoindol-2-yl)ethyl]-3-hydroxypentanoic acid (Compound No. 34), 5-(2',6'-Difluorobiphenyl-4-yl)-2-[2-(1,3-dioxo-1,3-dihydro-2H-isoindol-2-yl)ethyl]-3-hydroxypentanoic acid (Compound No. 35), 2-[2-(1,3-Dioxo-1,3-dihydro-2H-isoindol-2-yl)ethyl]-5-(4'-fluorobiphenyl-4-yl)-3-hydroxypentanoic acid (Compound No. 36), 5-(3',5'-Difluorobiphenyl-4-yl)-2-[2-(1,3-dioxo-1,3-dihydro-2H-isoindol-2-yl)ethyl]-3-hydroxypentanoic acid (Compound No. 37), 5-(3'-Chloro-4'-fluorobiphenyl-4-yl)-2-[2-(1,3-dioxo-1,3-dihydro-2H-isoindol-2-yl)ethyl]-3-hydroxypentanoic acid (Compound No. 38), 5-(3',4'-Dimethoxybiphenyl-4-yl)-2-[2-(1,3-dioxo-1,3-dihydro-2H-isoindol-2-yl)ethyl]-3-hydroxypentanoic acid (Compound No. 39), 5-(3'-Chlorobiphenyl-4-yl)-2-[2-(1,3-dioxo-1,3-dihydro-2H-isoindol-2-yl)ethyl]-3-hydroxypentanoic acid (Compound No. 40), 2-[2-(1,3-Dioxo-1,3-dihydro-2H-isoindol-2-yl)ethyl]-3-hydroxy-5-(3'-methylbiphenyl-4-yl)pentanoic acid (Compound No. 41), 5-(2',3'-Difluorobiphenyl-4-yl)-2-[2-(1,3-dioxo-1,3-dihydro-2H-isoindol-2-yl)ethyl]-3-hydroxypentanoic acid (Compound No. 42), 2-[2-(1,3-Dioxo-1,3-dihydro-2H-isoindol-2-yl)ethyl]-5-(2'-fluoro-3'-methoxybiphenyl-4-yl)-3-hydroxypentanoic acid (Compound No. 43), 2-[2-(1,3-Dioxo-1,3-dihydro-2H-isoindol-2-yl)ethyl]-5-(3'-fluoro-4'-methylbiphenyl-4-yl)-3-hydroxypentanoic acid (Compound No. 44), 2-[2-(1,3-Dioxo-1,3-dihydro-2H-isoindol-2-yl)ethyl]-3-hydroxy-5-(4'-hydroxybiphenyl-4-yl)pentanoic acid (Compound No. 50), 3-Hydroxy-5-(4'-methoxybiphenyl-4-yl)-2-[2-(3-methyl-2,6-dioxo-3,6-dihydropyrimidin-1(2H)-yl)ethyl]pentanoic acid (Compound No. 51), 5-(4'-Chlorobiphenyl-4-yl)-3-hydroxy-2-[2-(3-methyl-2,6-dioxo-3,6-dihydropyrimidin-1(2H)-yl)ethyl]pentanoic acid (Compound No. 52), 5-(4'-Fluorobiphenyl-4-yl)-3-hydroxy-2-[2-(3-methyl-2,6-dioxo-3,6-dihydropyrimidin-1(2H)-yl)ethyl]pentanoic acid (Compound No. 53), 5-[4-(5-Chloro-2-thienyl)phenyl]-2-[2-(1,3-dioxo-1,3-dihydro-2H-isoindol-2-yl)ethyl]-3-hydroxypentanoic acid (Compound No. 54), 4'-[4-Carboxy-6-(1,3-dioxo-1,3-dihydro-2H-isoindol-2-yl)-3-hydroxyhexyl]biphenyl-4-carboxylic acid (Compound No. 55), 2-[2-(1,3-Dioxo-1,3-dihydro-2H-isoindol-2-yl)ethyl]-3-hydroxy-5-[4'-(methoxycarbonyl)biphenyl-4-yl]pentanoic acid (Compound No. 56), 2-[2-(1,3-Dioxo-1,3-dihydro-2H-isoindol-2-yl)ethyl]-3-hydroxy-5-[4'-(trifluoromethyl)biphenyl-4-yl]pentanoic acid (Compound No. 57), 2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 58), 3-Hydroxy-2-[2-(4-oxo-1,2,3-benzotriazin-3(4H)-yl)ethyl]-5-[4'-(trifluoromethyl)biphenyl-4-yl]pentanoic acid (Compound No. 59), 5-(3',4'-Difluorobiphenyl-4-yl)-3-hydroxy-2-[2-(4-oxo-1,2,3-benzotriazin-3(4H)-yl)ethyl]pentanoic acid (Compound No. 60), 2-[2-(1,3-Dioxo-1,3-dihydro-2H-isoindol-2-yl)ethyl]-5-(3'-fluorobiphenyl-4-yl)-3-hydroxypentanoic acid (Compound No. 61), 5-[4'-(Benzyloxy)-3'-fluorobiphenyl-4-yl]-2-[2-(1,3-dioxo-1,3-dihydro-2H-isoindol-2-yl)ethyl]-3-hydroxypentanoic acid (Compound No. 62), 5-[4'-(Benzyloxy)biphenyl-4-yl]-2-[2-(1,3-dioxo-1,3-dihydro-2H-isoindol-2-yl)ethyl]-3-hydroxypentanoic acid (Compound No. 63), 3-Hydroxy-5-(4'-methoxybiphenyl-4-yl)-2-[2-(4-oxo-1,2,3-benzotriazin-3(4H)-yl)ethyl]pentanoic acid (Compound No. 64), 5-(4'-Chlorobiphenyl-4-yl)-3-hydroxy-2-[2-(4-oxo-1,2,3-benzotriazin-3(4H)-yl)ethyl]pentanoic acid (Compound No. 65), 2-[2-(1,3-Dioxo-1,3-dihydro-2H-isoindol-2-yl)ethyl]-3-hydroxy-5-(4'-methylbiphenyl-4-yl)pentanoic acid (Compound No. 66), 3-Hydroxy-5-[4-(6-methoxypyridin-3-yl)phenyl]-2-[2-(4-oxo-1,2,3-benzotriazin-3(4H)-yl)ethyl]pentanoic acid (Compound No. 67), 3-Hydroxy-5-(4'-methylbiphenyl-4-yl)-2-[2-(5-methyl-1,3-dioxo-1,3-dihydro-2H-isoindol-2-yl)ethyl]pentanoic acid (Compound No. 68), 5-(4'-Chlorobiphenyl-4-yl)-3-hydroxy-2-[2-(5-methyl-1,3-dioxo-1,3-dihydro-2H-isoindol-2-yl)ethyl]pentanoic acid (Compound No. 69), 3-Hydroxy-2-[2-(4-oxo-1,2,3-benzotriazin-3(4H)-yl)ethyl]-5-[4'-(trifluoromethoxy)biphenyl-4-yl]pentanoic acid (Compound No. 70), 5-(4'-Fluorobiphenyl-4-yl)-3-hydroxy-2-[2-(4-oxo-1,2,3-benzotriazin-3(4H)-yl)ethyl]pentanoic acid (Compound No. 71), 3-Hydroxy-5-(4'-methylbiphenyl-4-yl)-2-[2-(4-oxo-1,2,3-benzotriazin-3(4H)-yl)ethyl]pentanoic acid (Compound No. 72), 5-(4'-Cyanobiphenyl-4-yl)-3-hydroxy-2-[2-(4-oxo-1,2,3-benzotriazin-3(4H)-yl)ethyl]pentanoic acid (Compound No. 73), 5-(4'-Fluorobiphenyl-4-yl)-3-hydroxy-2-[2-(5-methyl-1,3-dioxo-1,3-dihydro-2H-isoindol-2-yl)ethyl]pentanoic acid (Compound No. 74), 3-Hydroxy-5-[4-(6-methoxypyridin-3-yl)phenyl]-2-[2-(5-methyl-1,3-dioxo-1,3-dihydro-2H-isoindol-2-yl)ethyl] pentanoic acid (Compound No. 75), 5-(4'-Ethylbiphenyl-4-yl)-3-hydroxy-2-[2-(4-oxo-1,2,3-benzotriazin-3(4H)-yl)ethyl]pentanoic acid (Compound No. 76), 3-Hydroxy-2-[2-(5-methyl-1,3-dioxo-1,3-dihydro-2H-isoindol-2-yl)ethyl]-5-[4'-trifluoromethyl)biphenyl-4-yl] pentanoic acid (Compound No. 77), 2-[2-(5-tert-Butyl-1,3-dioxo-1,3-dihydro-2H-isoindol-2-yl) ethyl]-3-hydroxy-5-[4-(6-methoxypyridin-3-yl)phenyl] pentanoic acid (Compound No. 97), 5-{4-[6-(Dimethylamino)pyridin-3-yl]phenyl}-2-[2-(1,3-dioxo-1,3-dihydro-2H-isoindol-2-yl)ethyl]-3-hydroxypentanoic acid (Compound No. 98), 2-[2-(1,3-Dioxo-1,3-dihydro-2H-isoindol-2-yl)ethyl]-3-hydroxy-5-[4'-(methylsulfonyl)biphenyl-4-yl]pentanoic acid (Compound No. 99), 5-[4'-(Aminocarbonyl)biphenyl-4-yl]-2-[2-(1,3-dioxo-1,3-dihydro-2H-isoindol-2-yl)ethyl]-3-hydroxypentanoic acid (Compound No. 100), 5-[4-(1-Benzyl-1H-pyrazol-4-yl)phenyl]-2-[2-(1,3-dioxo-1,3-dihydro-2H-isoindol-2-yl)ethyl]-3-hydroxypentanoic acid (Compound No. 101), 2-[2-(5-tert-Butyl-1,3-dioxo-1,3-dihydro-2H-isoindol-2-yl) ethyl]-5-(3',4'-difluorobiphenyl-4-yl)-3-hydroxypentanoic acid (Compound No. 105), 2-[2-(1,3-Dioxo-1,3-dihydro-2H-isoindol-2-yl)ethyl]-5-(3'-fluoro-4'-methoxybiphenyl-4-yl)-3-hydroxypentanoic acid (Compound No. 110), and 2-[2-(1,3-Dioxo-1,3-dihydro-2H-isoindol-2-yl)ethyl]-3-hydroxy-5-(4-pyrimidin-5-ylphenyl)pentanoic acid (Compound No. 119).

Scheme III, Path a Procedure:

Example 3

Synthesis of 2-(2-{[(benzyloxy)carbonyl] amino}ethyl)-5-biphenyl-4-yl-3-hydroxypentanoic acid (Compound No. 11)

Step 1: Synthesis of tert-butyl 2-(2-{[(benzyloxy) carbonyl]amino}ethyl)-5-biphenyl-4-yl-3-oxopentanoate To a solution of the compound tert-butyl 5-biphenyl-4-yl-3-oxopentanoate (237 mg,) in tetrahydrofuran (4 ml) and tert-butyl alcohol (4 ml) at 0° C. under inert atmosphere was added potassium tert-butoxide (98 mg) and stirred for 20 minutes. To this at 0° C. was then added n-tetrabutylammonium iodide (27 mg) and benzyl aziridine-1-carboxylate (130 mg) and stirred the reaction mixture for 5 minutes. The resulting reaction mixture was warmed to room temperature and then further heated at 70° C. for 2 hours. The solvent was evaporated under reduced pressure and the residue thus obtained was taken in water and extracted with ethyl acetate. The combined organic layers were washed with water and brine, dried over anhydrous sodium sulphate and concentrated under reduced pressure. The residue thus obtained was purified by column chromatography using 20% ethyl acetate in hexane as eluant to furnish the title compound (60 mg).

Step 2: Synthesis of tert-butyl 2-(2-{[(benzyloxy) carbonyl]amino}ethyl)-5-biphenyl-4-yl-3-hydroxy-pentanoate To a solution of the compound (100 mg) obtained from step 1 above in methanol (2 ml) at −10° C. to −2° C. was added sodium borohydride (9 mg) and stirred the mixture for 40 minutes at the same temperature. The solvent was evaporated under reduced pressure and the residue thus obtained was quenched with saturated solution of ammonium chloride and extracted with ethyl acetate. The combined organic layers were washed with water and brine, dried over anhydrous sodium sulphate and concentrated under reduced pressure. The residue thus obtained was purified by column chromatography using 5% methanol in dichloromethane as eluant to furnish the title compound (80 mg).

Step 3: Synthesis of 2-(2-{[(benzyloxy)carbonyl] amino}ethyl)-5-biphenyl-4-yl-3-hydroxypentanoic acid To a solution of the compound (40 mg) obtained from step 2 above in dry dichloromethane (10 ml) at 0° C. was added trifluoroacetic acid (0.5 ml) and anisole (0.05 ml) and stirred for 4 hours. The solvent and excess reagents were evaporated under reduced pressure and the residue thus obtained was purified by column chromatography using 60% ethyl acetate in hexane as eluant to furnish the title compound (25 mg).

Mass (m/z): 448.1 (M$^+$+1).

Scheme III, Path b Procedure:

Example 4

Synthesis of 5-biphenyl-4-yl-2-(2-{[(4-fluorophenyl) sulfonyl]amino}ethyl)-3-hydroxypentanoic acid (Compound No. 87)

Step 1: Synthesis of 4-{[(benzyloxy)carbonyl] amino}-1-(2-biphenyl-4-ylethyl)-2-(tert-butoxycarbonyl)butyl benzoate Benzoic acid (48.5 mg), 4-dimethylaminopyridine (24.3 mg) and triethylamine (0.08 ml) were added to a solution of tert-butyl 2-(2-{[(benzyloxy)carbonyl]amino}ethyl)-5-biphenyl-4-yl-3-hydroxypentanoate (200 mg) in dichloromethane (5 ml) at 0° C. and the reaction mixture was stirred for 15 minutes. 1-Ethyl-3-(3'-dimethylaminopropyl)-carbodiimide (152 mg) was added and the reaction mixture was stirred overnight. The reaction mixture was taken in distill water and extracted with dichloromethane (20 ml). The organic layer was washed with dilute sodium bicarbonate solution, brine solution, dried over anhydrous sodium sulphate and evaporated under vacuum. The residue thus obtained was purified by column chromatography using 10% ethyl acetate in hexane as eluent to furnish the title compound (180 mg).

Step 2: Synthesis of 4-amino-1-(2-biphenyl-4-yl-ethyl)-2-(tert-butoxycarbonyl)butyl benzoate 10% Palladium on charcoal (100 mg) was added to the solution of the compound (170 mg) obtained from the step 1 above in ethyl acetate (10 ml) and the reaction mixture was shaken under hydrogen atmosphere (40 psi) for 4 hours followed by filtration through celite. The filtrate was then concentrated under reduced pressure to furnish the title compound (100 mg).

Step 3: Synthesis of 1-(2-biphenyl-4-ylethyl)-2-(tert-butoxycarbonyl)-4-{[(4-fluorophenyl)sulfonyl]amino}butyl benzoate 4-Fluorobenzene sulphonylchloride (62 mg) and triethyl amine were added at 0° C. to the solution of the compound (150 mg) obtained from the step 2 above in dichloromethane (5 ml) and the reaction mixture was stirred for 3 hours. The reaction mixture was diluted with distilled water and extracted with dichloromethane (15 ml). The organic layer was washed with water, cold dilute hydrochloric acid and brine solution, dried over anhydrous sodium sulphate and evaporated under reduced pressure. The residue thus obtained was purified by column chromatography using 10% ethylacetate in hexane as eluent to furnish the title compound (100 mg).

Step 4: Synthesis of tert-butyl 5-biphenyl-4-yl-2-(2-{[(4-fluorophenyl)sulfonyl]amino}ethyl)-3-hydroxypentanoate Aqueous solution of lithium hydroxide (18 mg in 1 ml of water) was added to a solution of the compound (100 mg) obtained from Step 3 above in tetrahydrofuran:methanol:water (3:1:1, 5 ml). The resulting reaction mixture was stirred overnight. The reaction mixture was concentrated and the residue thus obtained was diluted with water, acidified with dilute hydrochloric acid solution and extracted with ethyl acetate. The organic layer was washed with distilled water and brine solution, dried over anhydrous sodium sulphate and concentrated under reduced pressure to furnish the title compound (94 mg).

Step 5: Synthesis of 5-biphenyl-4-yl-2-(2-{[(4-fluorophenyl)sulfonyl]amino}ethyl)-3-hydroxypentanoic acid Trifluoroacetic acid (0.5 ml) was added to the solution of the compound (100 mg) obtained from the step 4 above in dichloromethane (5 ml) and the reaction mixture was stirred for 2 hours. The reaction mixture was then concentrated. The residue was flushed with nitrogen gas and dried on high vacuum and purified by preparative thin layer chromatography using 12% methanol in dichloromethane to furnish the title compound (30 mg).

Mass (m/z): 494.1 ($M^+ + 23$)

Example 5

Synthesis of 5-biphenyl-4-yl-2-(2-{[(3-fluorophenyl)acetyl]amino}ethyl)-3-hydroxypentanoic acid (Compound No. 88)

Step 1: Synthesis of 1-(2-biphenyl-4-ylethyl)-2-(tert-butoxycarbonyl)-4-[(4-fluorobenzoyl)amino]butyl benzoate 4-Fluorobenzoic acid (45 mg), N-methylmorpholine (0.05 ml), hydroxybenzotriazole (51.5 mg) were added to the solution of 4-amino-1-(2-biphenyl-4-ylethyl)-2-(tert-butoxycarbonyl)butyl benzoate (150 mg) obtained from Example 3, step 2 in dry dimethylformamide (2 ml) at 0° C., 1-ethyl-3-(3'-dimethylaminopropyl)-carbodiimide (92 mg) was added and the reaction mixture was stirred overnight. The reaction mixture was taken in distilled water and extracted with ethylacetate. The organic layer was washed with distilled water and brine solution and dried over anhydrous sodium sulphate followed by evaporation under reduced pressure. The residue thus obtained was purified by column chromatography using 10% ethyl acetate in hexane as eluent to get the title compound (120 mg).

Step 2: Synthesis of tert-butyl 5-biphenyl-4-yl-2-{2-[(4-fluorobenzoyl)amino]ethyl}-3-hydroxypentanoate Aqueous solution of lithium hydroxide (22 mg) was added to a solution of the compound (120 mg) obtained from Step 1 above, in tetrahydrofuran:methanol:water (3:1:1, 5 ml) and the reaction mixture was stirred overnight. The reaction mixture was concentrated and the residue thus obtained was taken in distilled water, acidified with dilute hydrochloric acid solution and extracted with ethyl acetate. The organic layer was washed with distilled water and brine solution and dried over anhydrous sodium sulphate. The solvent was evaporated under reduced pressure to furnish the title compound (100 mg).

Step 3: Synthesis of 5-biphenyl-4-yl-2-{2-[(4-fluorobenzoyl)amino]ethyl}-3-hydroxypentanoic acid Trifluoroacetic acid (0.5 ml) was added to a solution of the compound obtained from the step 2 above (100 mg) in dichloromethane (5 ml) and the reaction mixture was stirred for 2 hours. The reaction mixture was then concentrated. The residue was flushed with nitrogen gas and dried on high vacuum and purified by preparative thin layer chromatography using 12% methanol in dichloromethane to furnish the title compound (30 mg).

Mass (m/z): 458.1 ($M^+ + 23$).

The following illustrative analogues were prepared analogously,

5-Biphenyl-4-yl-3-hydroxy-2-{2-[(phenylacetyl)amino]ethyl}pentanoic acid (Compound No. 45), and
5-Biphenyl-4-yl-2-{2-[(4-fluorobenzoyl)amino]ethyl}-3-hydroxypentanoic acid (Compound No. 89)

Example 6

Synthesis of 5-biphenyl-4-yl-2-[2-({[(4-fluorophenyl)amino]carbonyl}amino)ethyl]-3-hydroxypentanoic acid (Compound No. 92)

Step 1: Synthesis of 1-(2-biphenyl-4-ylethyl)-2-(tert-butoxycarbonyl)-4-({[(4-fluorophenyl)amino]carbonyl}amino)butyl benzoate 4-Fluorophenyl isocyanate (29 mg) was added to the solution of 4-amino-1-(2-biphenyl-4-ylethyl)-2-(tert-butoxycarbonyl)butyl benzoate (100 mg) obtained from Example 3, step 2 in dry dichloromethane at 0° C. under argon atmosphere and the reaction mixture stirred for 1 hour. The reaction mixture was dried over high vacuum to furnish the title compound (130 mg).

Step 2: Synthesis of 5-biphenyl-4-yl-2-[2-({[(4-fluorophenyl)amino]carbonyl}amino)ethyl]-3-hydroxypentanoic acid Aqueous solution of lithium hydroxide (22 mg in 1 ml) was added to the solution of the compound (130 mg) obtained from Step 1 above, in tetrahydrofuran:methanol:water (3:1:1, 5 ml) and the reaction mixture was stirred at 40° C. overnight. The reaction mixture was concentrated and the residue thus obtained was taken in distilled water, acidified with dilute hydrochloric acid solution and extracted with ethyl acetate. The organic layer was washed with distilled water and brine solution and dried over anhydrous sodium sulphate. The solvent was evaporated under reduced pressure to furnish the title compound (40 mg)

Mass (m/z): 473 (M$^+$+23); 451.1 (M+1)
Scheme IV, Procedure

Example 7

Synthesis of 5-biphenyl-4-yl-3-hydroxy-2-[2-(1-oxo-1,3-dihydro-2H-isoindol-2-yl)ethyl]pentanoic acid Compound No. 91

Step 1: Synthesis of tert-butyl 5-biphenyl-4-yl-2-[2-(1,3-dioxo-1,3-dihydro-2H-isoindol-2-yl)ethyl]-3-oxopentanoate The title compound was prepared following the procedure as depicted in Example 1, step 2, by using 2-(2-bromoethyl)-1H-isoindole-1,3(2H)-dione in place of 3-(2-bromoethyl)-1,2,3-benzotriazin-4(3H)-one.

Step 2: Synthesis of tert-butyl 5-biphenyl-4-yl-3-hydroxy-2-[2-(1-hydroxy-3-oxo-1,3-dihydro-2H-isoindol-2-yl)ethyl]pentanoate To a solution of the compound (165 mg) prepared from Step 1 above, in dry methanol and THF (1:1, 8 ml) at −20° C. was added sodium borohydride (38 mg) and the reaction mixture was stirred at rt for 3 h and then at 45° C. for 1 hour. The reaction mixture was cooled to 0° C. and quenched with saturated ammonium chloride solution. The solvents were evaporated in vacuo and the residue taken into water and extracted with ethyl acetate. The combined organic extracts were washed with water and brine and dried over anhydrous sodium sulfate. The solvent was evaporated under reduced pressure to obtain the crude title compound (165 mg).

Step 3: Synthesis of 5-biphenyl-4-yl-3-hydroxy-2-[2-(1-oxo-1,3-dihydro-2H-isoindol-2-yl)ethyl]pentanoic acid To a solution of the compound (160 mg) obtained from Step 2 above in trifluororacetic acid (2 ml) at room temperature was added sodium borohydride (36 mg) and stirred for 1 h. The volatiles were evaporated under reduced pressure and the residue purified by preparative TLC using 10% methanol-DCM as the mobile phase (100 mg).

Mass (m/z): 430.0 (M+1).
The following illustrative analogue was prepared analogously,
5-Biphenyl-4-yl-3-hydroxy-2-[2-(1-oxo-1,3-dihydro-2H-isoindol-2-yl)butyl]pentanoic acid (Compound No. 124).

Example 8

Separation of (2R,3S) & (2S,3R)-5-(4'-chlorobiphenyl-4-yl)-2-[2-(1,3-dioxo-1,3-dihydro-2H-isoindol-2-yl)ethyl]-3-hydroxypentanoic acid (Compound No. 80) and (2R,3R) & (2S,3S)-5-(4'-chlorobiphenyl-4-yl)-2-[2-(1,3-dioxo-1,3-dihydro-2H-isoindol-2-yl)ethyl]-3-hydroxypentanoic acid (Compound No. 81)

Compound No. 4 (30 mg) was loaded on preparative thin layer chromatography and the TLC plate was run using 30% acetone in dichloromethane as the mobile phase. The desired diastereomeric bands were cut separately. The silica gel of the individual bands containing the individual compound pairs was loaded on a short column and chromatographic purification by elution with 5% methanol in DCM yielded the corresponding title compounds. Compound No. 80: 6 mg. Compound No. 81:16 mg.

The following pairs of illustrative diastereomers were separated analogously,
(2R,3S+2S,3R)-2-[2-(1,3-Dioxo-1,3-dihydro-2H-isoindol-2-yl)ethyl]-5-(4'-formylbiphenyl-4-yl)-3-hydroxypentanoic acid (Compound No. 13),
(2R,3R+2S,3S)-2-[2-(1,3-Dioxo-1,3-dihydro-2H-isoindol-2-yl)ethyl]-5-(4'-formylbiphenyl-4-yl)-3-hydroxypentanoic acid (Compound No. 14),
(2R,3R+2S,3S)-2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 15),
(2R,3S+2S,3R)-2-[2-(1,3-Dioxo-1,3-dihydro-2H-isoindol-2-yl)ethyl]-3-hydroxy-5-(2',4',6'-trimethoxybiphenyl-4-yl)pentanoic acid (Compound No. 16),
(2R,3S+2S,3R)-5-(4'-Acetylbiphenyl-4-yl)-2-[2-(1,3-dioxo-1,3-dihydro-2H-isoindol-2-yl)ethyl]-3-hydroxypentanoic acid (Compound No. 17),
(2R,3R+2S,3S)-5-(4'-Acetylbiphenyl-4-yl)-2-[2-(1,3-dioxo-1,3-dihydro-2H-isoindol-2-yl)ethyl]-3-hydroxypentanoic acid (Compound No. 18),
(2R,3S+2S,3R)-2-[2-(1,3-Dioxo-1,3-dihydro-2H-isoindol-2-yl)ethyl]-3-hydroxy-5-(4'-propoxybiphenyl-4-yl)pentanoic acid (Compound No. 19),
(2R,3R+2S,3S)-2-[2-(1,3-Dioxo-1,3-dihydro-2H-isoindol-2-yl)ethyl]-3-hydroxy-5-(4'-propoxybiphenyl-4-yl)pentanoic acid (Compound No. 20),
(2R,3S+2S,3R)-5-(3',4'-Difluorobiphenyl-4-yl)-2-[2-(1,3-dioxo-1,3-dihydro-2H-isoindol-2-yl)ethyl]-3-hydroxypentanoic acid (Compound No. 21),
(2R,3R+2S,3S)-5-(3',4'-Difluorobiphenyl-4-yl)-2-[2-(1,3-dioxo-1,3-dihydro-2H-isoindol-2-yl)ethyl]-3-hydroxypentanoic acid (Compound No. 22),
(2R,3S+2S,3R)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 78),
(2R,3R+2S,3S)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 79),
(2R,3S+2S,3R)-2-[2-(1,3-Dioxo-1,3-dihydro-2H-isoindol-2-yl)ethyl]-5-(4'-fluorobiphenyl-4-yl)-3-hydroxypentanoic acid (Compound No. 82),
(2R,3R+2S,3S)-2-[2-(1,3-Dioxo-1,3-dihydro-2H-isoindol-2-yl)ethyl]-5-(4'-fluorobiphenyl-4-yl)-3-hydroxypentanoic acid (Compound No. 83),
(2R,3S+2S,3R)-2-[2-(5-tert-Butyl-1,3-dioxo-1,3-dihydro-2H-isoindol-2-yl)ethyl]-5-(4'-fluorobiphenyl-4-yl)-3-hydroxypentanoic acid (Compound No. 106),
(2R,3S+2S,3R)-2-[2-(5-tert-Butyl-1,3-dioxo-1,3-dihydro-2H-isoindol-2-yl)ethyl]-3-hydroxy-5-[4'-(trifluoromethyl)biphenyl-4-yl]pentanoic acid (Compound No. 107),
(2R,3R+2S,3S)-2-[2-(5-tert-Butyl-1,3-dioxo-1,3-dihydro-2H-isoindol-2-yl)ethyl]-5-(4'-fluorobiphenyl-4-yl)-3-hydroxypentanoic acid (Compound No. 108),
(2R,3R+2S,3S)-2-[2-(5-tert-Butyl-1,3-dioxo-1,3-dihydro-2H-isoindol-2-yl)ethyl]-3-hydroxy-5-[4'-(trifluoromethyl)biphenyl-4-yl]pentanoic acid (Compound No. 109),
2-[2-(1,3-Dioxo-1,3-dihydro-2H-isoindol-2-yl)ethyl]-5-(3'-fluoro-4'-methoxybiphenyl-4-yl)-3-hydroxypentanoic acid (Compound No. 110), (2R,3S+2S,3R)-2-[2-(1,3-Dioxo-1,3-dihydro-2H-isoindol-2-yl)ethyl]-3-hydroxy-5-[4-(6-methylpyridin-3-yl)phenyl]pentanoic acid (Compound No. 111), (2R,3R+2S,3S)-2-[2-(1,3-Dioxo-1,3-dihydro-2H-isoindol-2-yl)ethyl]-3-hydroxy-5-[4-(6-methylpyridin-3-yl)phenyl]pentanoic acid (Compound No. 112), (2R,3R+2S,3S)-2-[2-(5-tert-Butyl-1,3-dioxo-1,3-dihydro-2H-isoindol-2-yl)ethyl]-3-hydroxy-5-(4'-methylbiphenyl-4-yl)pentanoic acid (Compound No. 113), (2R,3S+2S,3R)-2-[2-(5-tert-Butyl-1,3-dioxo-1,3-dihydro-2H-isoindol-2-yl)ethyl]-3-hydroxy-5-(4'-methylbiphenyl-4-yl)pentanoic acid (Compound No. 114), (2R,3R+2S,3S)-2-[2-(5-tert-Butyl-1,3-dioxo-1,3-dihydro-2H-isoindol-2-yl)ethyl]-3-hydroxy-5-(4'-methoxybiphenyl-4-yl)pentanoic acid (Compound No. 115), (2R,3R+2S,3S)-2-[2-(5-tert-Butyl-1,3-dioxo-1,3-dihydro-2H-isoindol-2-yl)ethyl]-5-(4'-chlorobiphenyl-4-yl)-3-hydroxypentanoic acid (Compound No. 116), (2R,3S+2S,3R)-2-[2-(5-tert-Butyl-1,3-dioxo-1,3-dihydro-2H-isoindol-2-yl)ethyl]-5-(4'-chlorobiphenyl-4-yl)-3-hydroxypentanoic acid (Compound No. 117), (2R,3S+2S,3R)-2-[2-(5-tert-Butyl-1,3-dioxo-1,3-dihydro-2H-isoindol-2-yl)ethyl]-3-hydroxy-5-(4'-methoxybiphenyl-4-yl)pentanoic acid (Compound No. 118), (2R,3R+2S,3S)-5-biphenyl-4-yl-3-hydroxy-2-[2-(1H-indol-3-yl)ethyl]pentanoic acid (Compound No. 122), and (2R,3S+2S,3R)-5-biphenyl-4-yl-3-hydroxy-2-[2-(1H-indol-3-yl)ethyl]pentanoic acid (Compound No. 123).

Chiral HPLC analysis/separation was carried out for example, using Waters HPLC LC Module I Plus system with UV 486 detector using a Chiralcel OJ-H (250*4.6) column; mobile phase: 60:40 of 0.1% TFA in hexane:ethanol; flow rate 0.7 mL/min, run time 60 minutes.

The following illustrative single diastereomers were separated using chiral HPLC conditions, (2R,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 125), (2S,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 126), (2R,3R)-5-(4'-Chlorobiphenyl-4-yl)-2-[2-(1,3-dioxo-1,3-dihydro-2H-isoindol-2-yl)ethyl]-3-hydroxypentanoic acid (Compound No. 127), (2S,3S)-5-(4'-Chlorobiphenyl-4-yl)-2-[2-(1,3-dioxo-1,3-dihydro-2H-isoindol-2-yl)ethyl]-3-hydroxypentanoic acid (Compound No. 128), (2R,3S)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 129), (2S,3R)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 130), (2R,3R)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 131), (2S,3S)-2-[2-(1,3-Dioxo-1,3-dihydro-2H-isoindol-2-yl)ethyl]-3-hydroxy-5-[4-(6-methoxypyridin-3-yl)phenyl]pentanoic acid (Compound No. 132), (2R,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 133), (2S,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 134), (2R,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 135), and (2S,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 136).

Assay for Matrix Metallo Proteinases (MMPs)

NCEs/standards were prepared (stock 10 mM) in 100% DMSO and subsequent dilutions were made in 50% DMSO-50% TCNB (50 mM Tris, 10 mM $CaCl_2$, 150 mM NaCl, 0.05% Brij-35, pH 7.5). 1 µl of the compound and 88 µl of TCNB was added to wells of 96 well plate to achieve the desired final concentration of NCE (final DMSO concentration should not exceed 0.5%). 1 µl of activated, recombinant MMPs was added to each well (20-100 ng/100 µl reaction mixture) except the "negative well". (MMP-1, 9 &14 enzymes require prior activation. For this, supplied enzyme was incubated with either APMA, final concentration 1 mM, for a time period of 1 hr at 37° C.). Incubation was done at room temperature for 4-5 min. Reaction was initiated with 10 µl of 100 µM substrate (ES001: Aliquots were freshly diluted in TCNB; stock: 2 mM) and increase in florescence was monitored at excitation wavelength 320 nm followed by emission at 405 nm for 25-30 cycles. Increase in florescence (RFU) was calculated for positive, negative and NCE/standard wells. The percent inhibition compared to controls was calculated and $IC_{50}$ values determined using Graph-prism software.

Activities for MM9 provided $IC_{50}$ values from about 10 micromolar to about 2 nM, or from about 1 micromolar to about 2 nM, or from about 650 nM to about 2 nM, or from about 300 nM to about 2 nM, or from about 100 nM to about 2 nM, or from about 50 nM to about 2 nM, or from about 30 nM to about 2 nM, or from about 20 nM to about 2 nM, or from about 15 to about 2 nM, as compared to about 1.5 nM for marimasat.

Activities for MM12 provided $IC_{50}$ values from about 10 micromolar to about 0.4 nM, or from about 1 micromolar to about 0.4 nM, or from about 300 nM to about 0.4 nM, or from about 100 nM to about 0.4 nM, or from about 50 nM to about 0.4 nM, or from about 30 nM to about 0.4 nM, or from about 20 nM to about 0.4 nM, or from about 15 to about 0.4 nM, or from about 7 to about 0.4 nM as compared to about 0.9 nM for marimasat.

We claim:
1. A compound of Formula Ic:

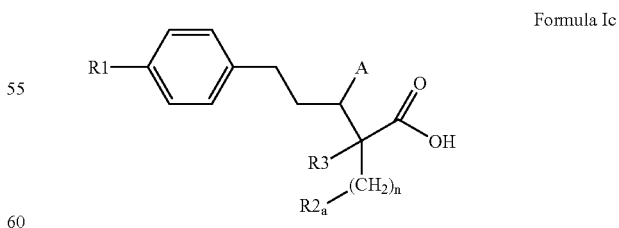

Formula Ic or racemates, enantiomers, diastereomers, or pharmaceutically acceptable salts thereof wherein:
n is an integer from 1 to 5;
$R_1$ is alkyl, alkenyl, alkynyl, cycloalkyl, aryl, heterocyclyl, heteroaryl, aralkyl, alkoxy, aryloxy, alkenyloxy or alkynyloxy, each of which can be optionally substituted;

$R_{2a}$ is $NR_4R_5$, —NHC(=Y)$R_4$, —NHC(=Y)$NR_5R_x$, —NHC(=O)$OR_4$, —$NHSO_2R_4$, amidino or guanidino; wherein:

Y is oxygen or sulphur;

$R_4$ is alkyl, alkenyl, alkynyl, cycloalkyl, aryl, heterocyclyl, heteroaryl, aralkyl, heteroarylalkyl, heterocyclylalkyl or cycloalkylalkyl;

m is an integer 0-2;

$R_5$ is hydrogen or $R_4$; or $R_4$ and $R_5$ together may optionally form a heterocyclic ring

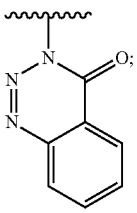

$R_x$ is $R_4$ or —$SO_2N(R_4)_2$; and

A is OH, $OR_4$, —OC(=O)$NR_4R_5$, O-acyl, $NH_2$, $NR_4R_5$, —NHC(=Y)$R_4$, —NHC(=Y)$NR_5R_x$, NHC(=O)$OR_4$, $NHSO_2R_4$.

2. A compound according to claim 1 which is:

5-Biphenyl-4-yl-3-hydroxy-2-[2-(4-oxo-1,2,3-benzotriazin-3(4H)-yl)ethyl]pentanoic acid (Compound No. 1), 2-(2-{[(Benzyloxy)carbonyl]amino}ethyl)-5-biphenyl-4-yl-3-hydroxypentanoicacid (Compound No. 11), 5-Biphenyl-4-yl-3-hydroxy-2-{2-[(phenylacetyl)amino]ethyl}pentanoic acid (Compound No. 45), 3-Hydroxy-2-[2-(4-oxo-1,2,3-benzotriazin-3(4H)-yl)ethyl]-5-[4'-(trifluoromethyl)biphenyl-4-yl]pentanoic acid (Compound No. 59), 5-(3',4'-Difluorobiphenyl-4-yl)-3-hydroxy-2-[2-(4-oxo-1,2,3-benzotriazin-3(4H)-yl)ethyl]pentanoic acid (Compound No. 60), 3-Hydroxy-5-(4'-methoxybiphenyl-4-yl)-2-[2-(4-oxo-1,2,3-benzotriazin-3(4H)-yl)ethyl]pentanoic acid (Compound No. 64), 5-(4'-Chlorobiphenyl-4-yl)-3-hydroxy-2-[2-(4-oxo-1,2,3-benzotriazin-3(4H)-yl)ethyl]pentanoic acid (Compound No. 65), 3-Hydroxy-5-[4-(6-methoxypyridin-3-yl)phenyl]-2-[2-(4-oxo-1,2,3-benzotriazin-3(4H)-yl)ethyl]pentanoic acid (Compound No. 67), 3-Hydroxy-2-[2-(4-oxo-1,2,3-benzotriazin-3(4H)-yl)ethyl]-5-[4'-(trifluoromethoxy)biphenyl-4-yl]pentanoic acid (Compound No. 70), 5-(4'-Fluorobiphenyl-4-yl)-3-hydroxy-2-[2-(4-oxo-1,2,3-benzotriazin-3(4H)-yl)ethyl]pentanoic acid (Compound No. 71), 3-hydroxy-5-(4'-methylbiphenyl-4-yl)-2-[2-(4-oxo-1,2,3-benzotriazin-3(4H)-yl)ethyl]pentanoic acid (Compound No. 72), 5-(4'-Cyanobiphenyl-4-yl)-3-hydroxy-2-[2-(4-oxo-1,2,3-benzotriazin-3(4H)-yl)ethyl]pentanoic acid (Compound No. 73), 5-(4'-Ethylbiphenyl-4-yl)-3-hydroxy-2-[2-(4-oxo-1,2,3-benzotriazin-3(4H)-yl)ethyl]pentanoic acid (Compound No. 76), 5-Biphenyl-4-yl-2-(2-{[(4-fluorophenyl)sulfonyl]amino}ethyl)-3-hydroxypentanoic acid (Compound No. 87), 5-Biphenyl-4-yl-2-(2-{[(3-fluorophenyl)acetyl]amino}ethyl)-3-hydroxypentanoic acid (Compound No. 88), 5-Biphenyl-4-yl-2-{2-[(4-fluorobenzoyl)amino]ethyl}-3-hydroxypentanoic acid (Compound No. 89), 5-Biphenyl-4-yl-2-[2-({[(4-fluorophenyl)amino]carbonyl}amino)ethyl]-3-hydroxypentanoic acid (Compound No. 92), (2R,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 133), (2S,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 134), (2R,3R)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 135), or (2S,3S)-3-Hydroxy-5-[4-(6-methoxypyridin-3-yl)phenyl]-2-[2-(4-oxo-1,2,3-benzotriazin-3(4H)-yl)ethyl]pentanoic acid (Compound No. 136)

or racemates, enantiomers, diastereomers, or pharmaceutically acceptable salts thereof.

3. A pharmaceutical composition comprising therapeutically effective amount of a compound according to any one of claims 1 or 2 together with pharmaceutically acceptable carriers, excipients, or diluents.

4. A pharmaceutical composition according to claim 3 further comprising one or more additional active ingredients selected from:
a) anti-inflammatory agents selected from
  (i) nonsteroidal anti-inflammatory agents piroxicam, diclofenac, propionic acids, fenamates, pyrazolones, salicylates, PDE-4/p38 MAP Kinase/Cathepsin inhibitors,
  (ii) leukotrienes LTC4/LTD4/LTE4/LTB4-Inhibitors, 5-lipoxygenase inhibitors and PAF-receptor antagonists,
  (iii) Cox-2 inhibitors, (iv) MMP inhibitors, or (v) interleukin-I inhibitors;
b) antihypertensive agents selected from (i) ACE inhibitors, e.g., enalapril, lisinopril, valsartan, telmisartan and quinapril, (ii) angiotensin II receptor antagonists and agonists, e.g., losartan, candesartan, irbesartan, valsartan, and eprosartan, (iii) β-blockers, or (iv) calcium channel blockers; and
c) immunosuppressive agents selected from cyclosporine, azathioprine and methotrexate, anti-inflammatory corticosteroids.

5. A method of treatment of an animal or a human suffering from rheumatoid arthritis which comprises administering to the animal or human an effective amount of a compound according to claim 1 or 2.

6. A compound according to claim 1 having the structure of formula Ic:

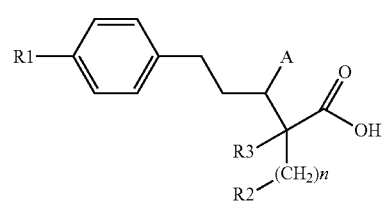

wherein $R_1$ is heteroaryl or aryl.

7. A compound according to claim 2 which is:
5-Biphenyl-4-yl-3-hydroxy-2-[2-(4-oxo-1,2,3-benzotriazin-3(4H)-yl)ethyl]pentanoic acid (Compound No. 1), or
2-(2-{[(Benzyloxy)carbonyl]amino}ethyl)-5-biphenyl-4-yl-3-hydroxypentanoicacid (Compound No. 11);
or racemates, enantiomers, diastereomers, or pharmaceutically acceptable salts thereof.

8. A compound according to claim 2 which is 3-Hydroxy-5-[4-(6-methoxypyridin-3-yl)phenyl]-2-[2-(4-oxo-1,2,3-benzotriazin-3(4H)-yl)ethyl]pentanoic acid or racemates, enantiomers, diastereomers, or pharmaceutically acceptable salts thereof.

9. A compound according to claim 2 which is (2S,3R)-3-Hydroxy-5-[4-(6-methoxypyridin-3-yl)phenyl]-2-[2-(4-oxo-1,2,3-benzotriazin-3(4H)-yl)ethyl]pentanoic acid or a pharmaceutically acceptable salt thereof.

* * * * *

UNITED STATES PATENT AND TRADEMARK OFFICE
CERTIFICATE OF CORRECTION

PATENT NO.        : 8,710,261 B2
APPLICATION NO.   : 11/816836
DATED             : April 29, 2014
INVENTOR(S)       : Venkata P. Palle et al.

Page 1 of 1

It is certified that error appears in the above-identified patent and that said Letters Patent is hereby corrected as shown below:

In the Specification

COLUMN 2, LINES 25-26:   "sclerodenna" should read -- scleroderma --

COLUMN 18, LINE 10:   "lane or triisoproplsilane" should read -- lane or triisopropylsilane) --

COLUMN 20, LINE 44:   "carbonate ot cesium carbonate" should read -- carbonate or cesium carbonate --

COLUMN 22, LINE 60:   "(wherein $R_F$ is" should read -- (wherein RF is --

COLUMN 24, LINE 24:   "Formula XXXI cab be" should read -- Formula XXXI can be --

COLUMN 31, LINE 39:   "scope of the present invention" should read -- scope of the present invention. --

COLUMN 42, LINE 39:   "(Compound No. 89)" should read -- (Compound No. 89). --

COLUMN 43, LINE 6:   "title compound (40 mg)" should read -- title compound (40 mg). --

In the Claims

COLUMN 48, CLAIM 6, LINE 54:
Formula Ic

" 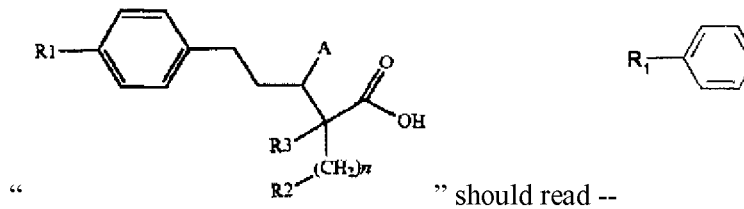 " should read -- 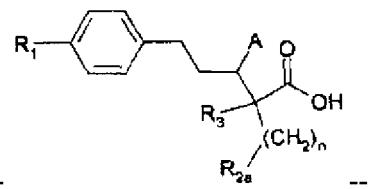 --

Signed and Sealed this
Twenty-seventh Day of January, 2015

Michelle K. Lee
*Deputy Director of the United States Patent and Trademark Office*